US009764035B2

(12) United States Patent
Shemi et al.

(10) Patent No.: US 9,764,035 B2
(45) Date of Patent: Sep. 19, 2017

(54) METHODS AND COMPOSITIONS FOR TREATING PROSTATE CANCER

(71) Applicant: Silenseed Ltd., Jerusalem (IL)

(72) Inventors: Amotz Shemi, Herzliya (IL); Elina Zorde Khvalevsky, Jerusalem (IL); Rachel Malka Gabai, Mata (IL)

(73) Assignee: SILENSEED LTD., Jerusalem (IL)

( * ) Notice: Subject to any disclaimer, the term of this patent is extended or adjusted under 35 U.S.C. 154(b) by 0 days.

(21) Appl. No.: 14/672,176

(22) Filed: Mar. 29, 2015

(65) Prior Publication Data

US 2015/0196648 A1 Jul. 16, 2015

Related U.S. Application Data

(63) Continuation of application No. 13/676,581, filed on Nov. 14, 2012, now Pat. No. 9,006,199.

(60) Provisional application No. 61/629,135, filed on Nov. 14, 2011.

(51) Int. Cl.

| *A61K 31/713* | (2006.01) |
|---|---|
| *A61K 9/70* | (2006.01) |
| *A61K 47/34* | (2017.01) |
| *A61K 9/00* | (2006.01) |
| *A61K 45/06* | (2006.01) |
| *A61N 5/10* | (2006.01) |
| *C12N 15/11* | (2006.01) |
| *C12N 15/113* | (2010.01) |
| *A61B 8/00* | (2006.01) |
| *A61B 10/02* | (2006.01) |
| *A61K 47/10* | (2017.01) |
| *A61K 47/26* | (2006.01) |
| *A61K 47/32* | (2006.01) |

(52) U.S. Cl.
CPC .......... *A61K 47/34* (2013.01); *A61B 8/4444* (2013.01); *A61B 10/0241* (2013.01); *A61K 9/0024* (2013.01); *A61K 9/0034* (2013.01); *A61K 9/7007* (2013.01); *A61K 31/713* (2013.01); *A61K 45/06* (2013.01); *A61K 47/10* (2013.01); *A61K 47/26* (2013.01); *A61K 47/32* (2013.01); *A61N 5/1001* (2013.01); *A61N 5/1007* (2013.01); *C12N 15/111* (2013.01); *C12N 15/113* (2013.01); *C12N 15/1135* (2013.01); *C12N 15/1138* (2013.01); *C12N 2310/111* (2013.01); *C12N 2310/14* (2013.01); *C12N 2310/3145* (2013.01); *C12N 2310/32* (2013.01); *C12N 2310/321* (2013.01); *C12N 2310/351* (2013.01); *C12N 2310/3513* (2013.01); *C12N 2310/3515* (2013.01); *C12N 2320/31* (2013.01); *C12N 2320/32* (2013.01)

(58) Field of Classification Search
USPC .......... 424/484, 425; 435/6, 6.14, 91.1, 455, 435/91.31, 6.1, 6.11, 6.12; 514/44; 536/23.1, 24.5, 24.31
See application file for complete search history.

(56) References Cited

U.S. PATENT DOCUMENTS

| 7,262,288 B1 * | 8/2007 | Cech .................... C12N 9/1241 435/183 |
|---|---|---|
| 7,691,997 B2 | 4/2010 | Khvorova |
| 8,889,642 B2 | 11/2014 | Shemi |
| 2003/0166588 A1 | 9/2003 | Iversen |
| 2005/0255487 A1 * | 11/2005 | Khvorova ............ A61K 31/713 435/6.11 |
| 2007/0167384 A1 * | 7/2007 | Leake .................... C12N 15/111 514/44 A |
| 2008/0076908 A1 * | 3/2008 | Khvorova ............ C12N 15/111 536/24.1 |
| 2008/0095761 A1 * | 4/2008 | Beachy .................. A61K 31/35 424/130.1 |
| 2008/0124370 A1 | 5/2008 | Marx |
| 2009/0004668 A1 | 1/2009 | Chen |
| 2009/0124569 A1 | 5/2009 | Bergan |
| 2010/0286241 A1 | 11/2010 | Xie |
| 2011/0195123 A1 | 8/2011 | Shemi |
| 2011/0224288 A1 * | 9/2011 | Zale .................... A61K 9/5153 514/449 |
| 2011/0275891 A1 | 11/2011 | Shemi |
| 2012/0022137 A1 * | 1/2012 | Rivers .................. A61K 9/0051 514/44 A |
| 2013/0142875 A1 | 6/2013 | Shemi |
| 2013/0324590 A1 | 12/2013 | Lin |

FOREIGN PATENT DOCUMENTS

| WO | 02/44321 | 6/2002 |
|---|---|---|
| WO | WO 2008/084643 | * 7/2008 |
| WO | 2009/108217 | 9/2009 |
| WO | 2010/001325 | 1/2010 |
| WO | 2011/062503 | 5/2011 |

OTHER PUBLICATIONS

Doench et al., Genes and Development, vol. 18, No. 5, pp. 504-511 (2004).
Holen et al., Nucleic Acids Res., vol. 30, No. 8, pp. 1757-1766 (2002).
Makadia et al, Polymers, vol. 3, pp. 1377-1397 (2011).
Li et al, Gene Therapy, vol. 19, pp. 775-780 (2012).
Brummelkamp et al. "Stable suppression of tumorigenicity by virus-mediated RNA interference" Cancer Cell, vol. 2, No. 3, pp. 243-247 (Sep. 2002).
Fleming et al. "Molecular consequences of silencing mutant K-ras in pancreatic cancer cells: Justification for K-ras directed therapy" Molecular Cancer Research, vol. 3, No. 7, pp. 413-423 (Jul. 2005).
Guo et al. "In situ vaccination with CD204 gene-silenced dendritic cell, not unmodified dendritic cell, enhances radiation therapy of prostate cancer" Molecular Cancer Therapeutics, vol. 11, No. 11, pp. 2331-2341 (Nov. 2012).

(Continued)

*Primary Examiner* — Jane Zara
(74) *Attorney, Agent, or Firm* — JMB Davis Ben-David

(57) ABSTRACT

Treatment of prostate cancer by regional and prolonged release of one or more nucleotide-based RNAi agents is provided.

18 Claims, 9 Drawing Sheets

(56) References Cited

OTHER PUBLICATIONS

Li et al. "Tumor vasculature is a key determinant for the efficiency of nanoparticle-mediated siRNA delivery" Gene Therapy, vol. 19, No. 7, pp. 775-780 (Jul. 2012).

Magzoub et al. "Interaction and structure induction of cell-penetrating peptides in the presence of phospholipid vesicles" Biochimica et Biopiysica Acta, vol. 1512, No. 1, pp. 77-89 (May 2001).

Makadia & Siegel "Poly lactic-co-glycolic acid (PLGA) as biodegradable controlled drug delivery carrier" Polymers, vol. 3, No. 3, pp. 1377-1397 (Aug. 2011).

Morioka et al. "Suppression of invasion of a hamster pancreatic cancer cell Line by antisense oligonucleotides mutation-matched to K-ras gene" In Vivo, vol. 19, No. 3, pp. 535-538 (May-Jun. 2005).

Normanno et al. "Implications for KRAS status and EGFR-targeted therapies in metastatic CRC" Nature Reviews Clinical Oncology, vol. 6, No. 9, pp. 519-527 (Sep. 2009).

Park et al. "Biodegradable polymers for microencapsulation of drugs" Molecules, vol. 10, No. 1, pp. 146-161 (Jan. 2005).

Patrawala et al. "Highly purified CD44.sup.+ prostate cancer cells from xenograft human tumors are enriched in tumorigenic and metastatic progenitor cells" Oncogene, vol. 25, No. 12, pp. 1696-1708 (Mar. 2006).

Pooga et al. "Cell penetration by transportan" FASEB Journal, vol. 12, No. 1, pp. 67-77 (Jan. 1998).

Rejiba et al. "K-ras oncogene silencing strategy reduces tumor growth and enhances gemcitabine chemotherapy efficacy for pancreatic cancer treatment" Cancer Science, vol. 98, No. 7, pp. 1128-1136 (Jul. 2007).

Singh et al. "A gene expression signature associated with 'K-ras addiction' reveals regulators of EMT and tumor cell survival" Cancer Cell, vol. 15, No. 6, pp. 489-500 (Jun. 2009).

Terrone et al. "Penetratin and related cell-penetrating cationic peptides can translocate across lipid bilayers in the presence of a transbilayer potential" Biochemistry, vol. 42, No. 47, pp. 13787-13799 (Dec. 2003).

\* cited by examiner

US 9,764,035 B2

SEQUENCE LISTING

<160> NUMBER OF SEQ ID NOS: 114

<210> SEQ ID NO 1
<211> LENGTH: 19
<212> TYPE: RNA
<213> ORGANISM: Homo sapiens

<400> SEQUENCE: 1
ugccagggac cauguuuug                                                19

<210> SEQ ID NO 2
<211> LENGTH: 19
<212> TYPE: RNA
<213> ORGANISM: Homo sapiens

<400> SEQUENCE: 2
cggaaauguu augaagcag                                                19

<210> SEQ ID NO 3
<211> LENGTH: 19
<212> TYPE: RNA
<213> ORGANISM: Homo sapiens

<400> SEQUENCE: 3
gcugaagaaa cuugguaau                                                19

<210> SEQ ID NO 4
<211> LENGTH: 19
<212> TYPE: RNA
<213> ORGANISM: Homo sapiens

<400> SEQUENCE: 4
ugauuuauac uucucuguu                                                19

<210> SEQ ID NO 5
<211> LENGTH: 19
<212> TYPE: RNA
<213> ORGANISM: Homo sapiens

<400> SEQUENCE: 5
ugauuuauac uucucuguu                                                19

<210> SEQ ID NO 6
<211> LENGTH: 19
<212> TYPE: RNA
<213> ORGANISM: Homo sapiens

<400> SEQUENCE: 6
augaauggaa ccagcaaca                                                19

<210> SEQ ID NO 7
<211> LENGTH: 22
<212> TYPE: RNA
<213> ORGANISM: Homo sapiens

<400> SEQUENCE: 7
cugagcaucg gauuugagac ug                                            22

<210> SEQ ID NO 8
<211> LENGTH: 19
<212> TYPE: RNA
<213> ORGANISM: Homo sapiens

<400> SEQUENCE: 8

-continued

| | |
|---|---|
| ggcgcagauc gauuugaau | 19 |

<210> SEQ ID NO 9
<211> LENGTH: 19
<212> TYPE: RNA
<213> ORGANISM: Homo sapiens

<400> SEQUENCE: 9

| | |
|---|---|
| aagagggccg agcgucuca | 19 |

<210> SEQ ID NO 10
<211> LENGTH: 19
<212> TYPE: RNA
<213> ORGANISM: Homo sapiens

<400> SEQUENCE: 10

| | |
|---|---|
| gaacguuccg cagagaaaa | 19 |

<210> SEQ ID NO 11
<211> LENGTH: 19
<212> TYPE: RNA
<213> ORGANISM: Homo sapiens

<400> SEQUENCE: 11

| | |
|---|---|
| gcacuuccuc uacuccuca | 19 |

<210> SEQ ID NO 12
<211> LENGTH: 19
<212> TYPE: RNA
<213> ORGANISM: Homo sapiens

<400> SEQUENCE: 12

| | |
|---|---|
| caccaagaag uucaucucc | 19 |

<210> SEQ ID NO 13
<211> LENGTH: 19
<212> TYPE: RNA
<213> ORGANISM: Homo sapiens

<400> SEQUENCE: 13

| | |
|---|---|
| caucgccagc aucaucaaa | 19 |

<210> SEQ ID NO 14
<211> LENGTH: 19
<212> TYPE: RNA
<213> ORGANISM: Homo sapiens

<400> SEQUENCE: 14

| | |
|---|---|
| gacucauauc caccaaaca | 19 |

<210> SEQ ID NO 15
<211> LENGTH: 19
<212> TYPE: DNA
<213> ORGANISM: Homo sapiens

<400> SEQUENCE: 15

| | |
|---|---|
| cagggagatt catgtggat | 19 |

<210> SEQ ID NO 16
<211> LENGTH: 19
<212> TYPE: DNA
<213> ORGANISM: Homo sapiens

```
<400> SEQUENCE: 16
gtcttggtcc ttctcatta                                              19

<210> SEQ ID NO 17
<211> LENGTH: 19
<212> TYPE: RNA
<213> ORGANISM: Homo sapiens

<400> SEQUENCE: 17
ggcauaccuu aaacaagcu                                              19

<210> SEQ ID NO 18
<211> LENGTH: 19
<212> TYPE: RNA
<213> ORGANISM: Homo sapiens

<400> SEQUENCE: 18
gacgacaaua agcucuuca                                              19

<210> SEQ ID NO 19
<211> LENGTH: 19
<212> TYPE: RNA
<213> ORGANISM: Homo sapiens

<400> SEQUENCE: 19
ccuuaugacc acucuagag                                              19

<210> SEQ ID NO 20
<211> LENGTH: 19
<212> TYPE: RNA
<213> ORGANISM: Homo sapiens

<400> SEQUENCE: 20
gaugagacac caauuauug                                              19

<210> SEQ ID NO 21
<211> LENGTH: 19
<212> TYPE: RNA
<213> ORGANISM: Homo sapiens

<400> SEQUENCE: 21
gccaaaacuu caaauccaa                                              19

<210> SEQ ID NO 22
<211> LENGTH: 19
<212> TYPE: RNA
<213> ORGANISM: Homo sapiens

<400> SEQUENCE: 22
ccacaagaac agcaagcac                                              19

<210> SEQ ID NO 23
<211> LENGTH: 19
<212> TYPE: RNA
<213> ORGANISM: Homo sapiens

<400> SEQUENCE: 23
cgacgacaug aauaagauc                                              19

<210> SEQ ID NO 24
<211> LENGTH: 19
<212> TYPE: RNA
<213> ORGANISM: Homo sapiens
```

```
<400> SEQUENCE: 24
ccaucagcua cccauauuc                                            19

<210> SEQ ID NO 25
<211> LENGTH: 19
<212> TYPE: RNA
<213> ORGANISM: Homo sapiens

<400> SEQUENCE: 25
ggaaggcaac cagcuguua                                            19

<210> SEQ ID NO 26
<211> LENGTH: 19
<212> TYPE: DNA
<213> ORGANISM: Homo sapiens

<400> SEQUENCE: 26
gctgagaacc aataccaga                                            19

<210> SEQ ID NO 27
<211> LENGTH: 19
<212> TYPE: RNA
<213> ORGANISM: Homo sapiens

<400> SEQUENCE: 27
caacucucag gcagugugu                                            19

<210> SEQ ID NO 28
<211> LENGTH: 19
<212> TYPE: RNA
<213> ORGANISM: Homo sapiens

<400> SEQUENCE: 28
cacgaaggcu gugcugcuu                                            19

<210> SEQ ID NO 29
<211> LENGTH: 19
<212> TYPE: RNA
<213> ORGANISM: Homo sapiens

<400> SEQUENCE: 29
cgugcuguga caccgacuu                                            19

<210> SEQ ID NO 30
<211> LENGTH: 19
<212> TYPE: RNA
<213> ORGANISM: Homo sapiens

<400> SEQUENCE: 30
ccaacgcagc cagcaccaa                                            19

<210> SEQ ID NO 31
<211> LENGTH: 19
<212> TYPE: RNA
<213> ORGANISM: Homo sapiens

<400> SEQUENCE: 31
cuggaaugcu caggaaugu                                            19

<210> SEQ ID NO 32
<211> LENGTH: 19
<212> TYPE: RNA
```

```
<213> ORGANISM: Homo sapiens

<400> SEQUENCE: 32
ccugaccucu gucuuacuu                                              19

<210> SEQ ID NO 33
<211> LENGTH: 19
<212> TYPE: RNA
<213> ORGANISM: Homo sapiens

<400> SEQUENCE: 33
cugggaagaa aucugagaa                                              19

<210> SEQ ID NO 34
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 34
ugccagggac cauguuugt t                                            21

<210> SEQ ID NO 35
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 35
caaaacaugg ucccuggcat t                                           21

<210> SEQ ID NO 36
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 36
cggaaauguu augaagcagt t                                           21

<210> SEQ ID NO 37
<211> LENGTH: 21
```

```
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 37
cugcuucaua acauuuccgt t                                            21

<210> SEQ ID NO 38
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 38
gcugaagaaa cuugguaaut t                                            21

<210> SEQ ID NO 39
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 39
auuaccaagu uucuucagct t                                            21

<210> SEQ ID NO 40
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 40
ugauuuauac uucucuguut t                                            21

<210> SEQ ID NO 41
```

```
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 41
aacagagaag uauaaaucat t                                              21

<210> SEQ ID NO 42
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 42
ugauuuauac uucucuguut t                                              21

<210> SEQ ID NO 43
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 43
aacagagaag uauaaaucat t                                              21

<210> SEQ ID NO 44
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 44
augaauggaa ccagcaacat t                                              21
```

```
<210> SEQ ID NO 45
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 45
augaauggaa ccagcaacat t                                     21

<210> SEQ ID NO 46
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 46
cugagcaucg gauuugagat t                                     21

<210> SEQ ID NO 47
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 47
ucucaaaucc gaugcucagt t                                     21

<210> SEQ ID NO 48
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 48
ggcgcagauc gauuugaaut t                                     21
```

```
<210> SEQ ID NO 49
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 49
ugagacgcuc ggcccucuut t                                            21

<210> SEQ ID NO 50
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 50
aagagggccg agcgucucat t                                            21

<210> SEQ ID NO 51
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 51
auucaaaucg aucugcgcct t                                            21

<210> SEQ ID NO 52
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 52
gaacguuccg cagagaaaat t                                            21
```

<210> SEQ ID NO 53
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 53
uuuucucugc ggaacguuct t          21

<210> SEQ ID NO 54
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 54
gcacuuccuc uacuccucat t          21

<210> SEQ ID NO 55
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 55
ugaggaguag aggaagugct t          21

<210> SEQ ID NO 56
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 56
caccaagaag uucaucucct t                                              21

<210> SEQ ID NO 57
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 57
ggagaugaac uucuuggugt t                                              21

<210> SEQ ID NO 58
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 58
caucgccagc aucaucaaat t                                              21

<210> SEQ ID NO 59
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 59
uuugaugaug cuggcgaugt t                                              21

<210> SEQ ID NO 60
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 60
gacucauauc caccaaacat t                                               21

<210> SEQ ID NO 61
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 61
uguuuggugg auaugaguct t                                               21

<210> SEQ ID NO 62
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 62
cagggagauu cauguggaut t                                               21

<210> SEQ ID NO 63
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 63
auccacauga aucucccugt t                                               21

<210> SEQ ID NO 64
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

```
<400> SEQUENCE: 64
gucuuggucc uucucauuat t                                              21

<210> SEQ ID NO 65
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 65
uaaugagaag gaccaagact t                                              21

<210> SEQ ID NO 66
<211> LENGTH: 19
<212> TYPE: RNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (3)..(3)
<223> OTHER INFORMATION: 2'-O-methyl modified residue
<220> FEATURE:
<221> NAME/KEY: misc_feature
<222> LOCATION: (13)..(13)
<223> OTHER INFORMATION: 2'-O-methyl modified residue
<220> FEATURE:
<221> NAME/KEY: misc_feature
<222> LOCATION: (16)..(16)
<223> OTHER INFORMATION: 2'-O-methyl modified residue

<400> SEQUENCE: 66
gcugaagaaa cuugguaau                                                 19

<210> SEQ ID NO 67
<211> LENGTH: 19
<212> TYPE: RNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (3)..(3)
<223> OTHER INFORMATION: 2'-O-methyl modified residue
<220> FEATURE:
<221> NAME/KEY: misc_feature
<222> LOCATION: (6)..(6)
<223> OTHER INFORMATION: 2'-O-methyl modified residue
<220> FEATURE:
<221> NAME/KEY: misc_feature
<222> LOCATION: (16)..(16)
<223> OTHER INFORMATION: 2'-O-methyl modified residue

<400> SEQUENCE: 67
auuaccaagu uucuucagc                                                 19

<210> SEQ ID NO 68
<211> LENGTH: 19
<212> TYPE: RNA
<213> ORGANISM: Artificial Sequence
<220> FEATURE:
<223> OTHER INFORMATION: siRNA sense strand
```

```
<220> FEATURE:
<221> NAME/KEY: misc_feature
<222> LOCATION: (5)..(5)
<223> OTHER INFORMATION: 2'-O-methyl modified residue
<220> FEATURE:
<221> NAME/KEY: misc_feature
<222> LOCATION: (7)..(7)
<223> OTHER INFORMATION: 2'-O-methyl modified residue
<220> FEATURE:
<221> NAME/KEY: misc_feature
<222> LOCATION: (11)..(11)
<223> OTHER INFORMATION: 2'-O-methyl modified residue
<220> FEATURE:
<221> NAME/KEY: misc_feature
<222> LOCATION: (14)..(14)
<223> OTHER INFORMATION: 2'-O-methyl modified residue
<220> FEATURE:
<221> NAME/KEY: misc_feature
<222> LOCATION: (18)..(18)
<223> OTHER INFORMATION: 2'-O-methyl modified residue

<400> SEQUENCE: 68
gacucauauc caccaaaca                                               19

<210> SEQ ID NO 69
<211> LENGTH: 19
<212> TYPE: RNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(1)
<223> OTHER INFORMATION: 2'-O-methyl modified residue
<220> FEATURE:
<221> NAME/KEY: misc_feature
<222> LOCATION: (5)..(5)
<223> OTHER INFORMATION: 2'-O-methyl modified residue
<220> FEATURE:
<221> NAME/KEY: misc_feature
<222> LOCATION: (8)..(8)
<223> OTHER INFORMATION: 2'-O-methyl modified residue
<220> FEATURE:
<221> NAME/KEY: misc_feature
<222> LOCATION: (14)..(14)
<223> OTHER INFORMATION: 2'-O-methyl modified residue

<400> SEQUENCE: 69
uguuuggugg auaugaguc                                               19

<210> SEQ ID NO 70
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 70
ggcauaccuu aaacaagcut t                                            21

<210> SEQ ID NO 71
<211> LENGTH: 21
<212> TYPE: DNA
<213> ORGANISM: Artificial Sequence
<220> FEATURE:
```

-continued

<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 71
agcuuguuua agguaugcct t                                              21

<210> SEQ ID NO 72
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 72
gacgacaaua agcucuucat t                                              21

<210> SEQ ID NO 73
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 73
ugaagagcuu auugucguct t                                              21

<210> SEQ ID NO 74
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 74
ccuuaugacc acucuagagt t                                              21

<210> SEQ ID NO 75
<211> LENGTH: 21
<212> TYPE: DNA
<213> ORGANISM: Artificial Sequence

```
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 75
cucuagagug gucauaaggt t                                              21

<210> SEQ ID NO 76
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 76
gaugagacac caauuauugt t                                              21

<210> SEQ ID NO 77
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 77
caauaauugg ugucucauct t                                              21

<210> SEQ ID NO 78
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 78
gccaaaacuu caaauccaat t                                              21

<210> SEQ ID NO 79
<211> LENGTH: 21
<212> TYPE: DNA
```

```
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 79
uuggauuuga aguuuggct t                                              21

<210> SEQ ID NO 80
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 80
ccacaagaac agcaagcact t                                             21

<210> SEQ ID NO 81
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 81
gugcuugcug uucuugtggt t                                             21

<210> SEQ ID NO 82
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 82
cgacgacaug aauaagauct t                                             21

<210> SEQ ID NO 83
<211> LENGTH: 21
```

```
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 83
gaucuuauuc augucgucgt t                                              21

<210> SEQ ID NO 84
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 84
ccaucagcua cccauauuct t                                              21

<210> SEQ ID NO 85
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 85
gaauaugggu agcugauggt t                                              21

<210> SEQ ID NO 86
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 86
ggaaggcaac cagcuguuat t                                              21

<210> SEQ ID NO 87
```

```
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 87
uaacagcugg uugccuucct t                                              21

<210> SEQ ID NO 88
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 88
gctgagaacc aataccagat t                                              21

<210> SEQ ID NO 89
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 89
tctggtattg gttctcagct t                                              21

<210> SEQ ID NO 90
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 90
caacucucag gcagugugut t                                              21
```

```
<210> SEQ ID NO 91
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 91
acacacugcc ugagaguugt t                                              21

<210> SEQ ID NO 92
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 92
cacgaaggcu gugcugcuut t                                              21

<210> SEQ ID NO 93
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 93
aagcagcaca gccuucgugt t                                              21

<210> SEQ ID NO 94
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 94
cgugcuguga caccgacuut t                                              21
```

```
<210> SEQ ID NO 95
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 95
aagucggugu cacagcacgt t                                              21

<210> SEQ ID NO 96
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 96
ccaacgcagc cagcaccaat t                                              21

<210> SEQ ID NO 97
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 97
uuggugcugg cugcguuggt t                                              21

<210> SEQ ID NO 98
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 98
cuggaaugcu caggaaugut t                                              21
```

```
<210> SEQ ID NO 99
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 99
acauuccuga gcauuccagt t                                              21

<210> SEQ ID NO 100
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 100
ccugaccucu gucuuacuut t                                              21

<210> SEQ ID NO 101
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 101
aaguaagaca gaggucaggt t                                              21

<210> SEQ ID NO 102
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 102
```
cugggaagaa aucugagaat t                                    21

<210> SEQ ID NO 103
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 103
uucucagauu ucuucccagt t                                    21

<210> SEQ ID NO 104
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (3)..(3)
<223> OTHER INFORMATION: 2'-O-methyl modified residue
<220> FEATURE:
<221> NAME/KEY: misc_feature
<222> LOCATION: (13)..(13)
<223> OTHER INFORMATION: 2'-O-methyl modified residue
<220> FEATURE:
<221> NAME/KEY: misc_feature
<222> LOCATION: (16)..(16)
<223> OTHER INFORMATION: 2'-O-methyl modified residue
<220> FEATURE:
<221> NAME/KEY: misc_feature
<222> LOCATION: (20)..(21)
<223> OTHER INFORMATION: DNA nucleotides

<400> SEQUENCE: 104
gcugaagaaa cuugguaaut t                                    21

<210> SEQ ID NO 105
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (3)..(3)
<223> OTHER INFORMATION: 2'-O-methyl modified residue
<220> FEATURE:
<221> NAME/KEY: misc_feature
<222> LOCATION: (6)..(6)
<223> OTHER INFORMATION: 2'-O-methyl modified residue
<220> FEATURE:
<221> NAME/KEY: misc_feature
<222> LOCATION: (16)..(16)
<223> OTHER INFORMATION: 2'-O-methyl modified residue
<220> FEATURE:
<221> NAME/KEY: misc_feature
<222> LOCATION: (20)..(21)
<223> OTHER INFORMATION: DNA nucleotides

<400> SEQUENCE: 105
auuaccaagu uucuucagct t                                              21

<210> SEQ ID NO 106
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (5)..(5)
<223> OTHER INFORMATION: 2'-O-methyl modified residue
<220> FEATURE:
<221> NAME/KEY: misc_feature
<222> LOCATION: (7)..(7)
<223> OTHER INFORMATION: 2'-O-methyl modified residue
<220> FEATURE:
<221> NAME/KEY: misc_feature
<222> LOCATION: (11)..(11)
<223> OTHER INFORMATION: 2'-O-methyl modified residue
<220> FEATURE:
<221> NAME/KEY: misc_feature
<222> LOCATION: (14)..(14)
<223> OTHER INFORMATION: 2'-O-methyl modified residue
<220> FEATURE:
<221> NAME/KEY: misc_feature
<222> LOCATION: (18)..(18)
<223> OTHER INFORMATION: 2'-O-methyl modified residue
<220> FEATURE:
<221> NAME/KEY: misc_feature
<222> LOCATION: (20)..(21)
<223> OTHER INFORMATION: DNA nucleotides

<400> SEQUENCE: 106
gacucauauc caccaaacat t                                              21

<210> SEQ ID NO 107
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (1)..(1)
<223> OTHER INFORMATION: 2'-O-methyl modified residue
<220> FEATURE:
<221> NAME/KEY: misc_feature
<222> LOCATION: (1)..(19)
<223> OTHER INFORMATION: RNA
<220> FEATURE:
<221> NAME/KEY: misc_feature
<222> LOCATION: (5)..(5)
<223> OTHER INFORMATION: 2'-O-methyl modified residue
<220> FEATURE:
<221> NAME/KEY: misc_feature
<222> LOCATION: (8)..(8)
<223> OTHER INFORMATION: 2'-O-methyl modified residue
<220> FEATURE:
<221> NAME/KEY: misc_feature
<222> LOCATION: (14)..(14)
<223> OTHER INFORMATION: 2'-O-methyl modified residue
<220> FEATURE:

```
<221> NAME/KEY: misc_feature
<222> LOCATION: (20)..(21)
<223> OTHER INFORMATION: DNA nucleotides

<400> SEQUENCE: 107
uguuuggugg auaugaguct t                                              21

<210> SEQ ID NO 108
<211> LENGTH: 21
<212> TYPE: DNA
<213> ORGANISM: Artificial Sequence
<220> FEATURE:
<223> OTHER INFORMATION: siRNA sense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 108
guuggagcug auggcguagt t                                              21

<210> SEQ ID NO 109
<211> LENGTH: 21
<212> TYPE: DNA
<213> ORGANISM: Artificial Sequence
<220> FEATURE:
<223> OTHER INFORMATION: siRNA antisense strand
<220> FEATURE:
<221> NAME/KEY: misc_feature
<222> LOCATION: (1)..(19)
<223> OTHER INFORMATION: RNA nucleotides
<220> FEATURE:
<221> NAME/KEY: misc_feature
<222> LOCATION: (20)..(21)
<223> OTHER INFORMATION: DNA nucleotides

<400> SEQUENCE: 109
cuacgccauc agcuccaact t                                              21

<210> SEQ ID NO 110
<211> LENGTH: 11
<212> TYPE: PRT
<213> ORGANISM: Human immunodeficiency virus type 1

<400> SEQUENCE: 110

Tyr Gly Arg Lys Lys Arg Arg Gln Arg Arg Arg
1               5                   10

<210> SEQ ID NO 111
<211> LENGTH: 27
<212> TYPE: PRT
<213> ORGANISM: Artificial Sequence
<220> FEATURE:
<223> OTHER INFORMATION: synthetic peptide chimera of galanin and
      mastoparan
<220> FEATURE:
<221> NAME/KEY: misc_feature
<222> LOCATION: (27)..(27)
<223> OTHER INFORMATION: amide_modification

<400> SEQUENCE: 111

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25
```

-continued

```
<210> SEQ ID NO 112
<211> LENGTH: 17
<212> TYPE: PRT
<213> ORGANISM: Artificial Sequence
<220> FEATURE:
<223> OTHER INFORMATION: synthetic peptide - hydrophobic domain fused to
      an NLS

<400> SEQUENCE: 112

Gly Ala Leu Phe Leu Gly Phe Leu Gly Ala Ala Gly Ser Thr Met Gly
1               5                   10                  15

Ala

<210> SEQ ID NO 113
<211> LENGTH: 12
<212> TYPE: PRT
<213> ORGANISM: Artificial Sequence
<220> FEATURE:
<223> OTHER INFORMATION: synthetic peptide

<400> SEQUENCE: 113

Lys Glu Thr Trp Trp Glu Thr Trp Trp Thr Glu Trp
1               5                   10

<210> SEQ ID NO 114
<211> LENGTH: 20
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: residue acylated at N-terminus
<220> FEATURE:
<221> NAME/KEY: misc_feature
<222> LOCATION: (20)..(20)
<223> OTHER INFORMATION: residue modified by attaching cysteamide at
      C-terminus

<400> SEQUENCE: 114

Gly Leu Trp Arg Ala Leu Trp Arg Leu Leu Arg Ser Leu Trp Arg Leu
1               5                   10                  15

Leu Trp Arg Ala
            20
```

METHODS AND COMPOSITIONS FOR TREATING PROSTATE CANCER

CROSS REFERENCE TO RELATED APPLICATIONS

This is a Continuation of co-pending U.S. patent application Ser. No. 13/676,581, filed Nov. 14, 2012, and which claims the benefit of U.S. Provisional Application No. 61/629,135, filed Nov. 14, 2011. The contents of the prior applications are incorporated herein by reference in their entirety.

FIELD

Treatment of prostate cancer by regional and prolonged release of one or more nucleotide-based RNAi agents is provided.

BACKGROUND

Prostate Cancer

Prostate cancer is cancer that starts in the prostate gland. It is the third most common cause of death from cancer in men of all ages and is the most common cause of death from cancer in men over age 75. Prostate cancer is rarely found in men younger than 40. Systemic chemotherapy is often ineffective in the treatment of prostate-confined cancer. In-vivo results from regional delivery of chemotherapy in prostate cancer (1) show potential higher efficiency in tumor arrest but still have major issues to be solved. Chemotherapy treatment requires large drug amounts, having toxicity comparable to the recommended dose of 60 to 80 mg/m$^2$ for intravenous administration. One general cause of anticancer drug resistance is the limited ability of drugs to penetrate tumor tissue and to reach all of the tumor cells in a potentially lethal concentration (2). Extravasation and interstitial transport (via diffusion and convection) are diminished in the intratumoral space by high interstitial pressure, hypovascularity, high tumor cell density and/or a large stroma fraction; these problems are more serious in larger, bulky tumors. Chemotherapy drugs are more effective against proliferating vs. quiescent cells; thus, slowly proliferating cells at greater distances from tumor blood vessels are likely to be resistant to therapy. Chemotherapeutic drugs also are typically inefficient against tumor stem cells.

Prostate-specific antigen (PSA) is a protein produced by cells of the prostate gland, whose level is reported as nanograms of PSA per milliliter (ng/mL) in the blood. While a PSA level below 4.0 ng/mL was previously considered normal, one large study showed the presence of prostate cancer in 15.2 percent of men with a PSA level of ≤4.0 ng/mL (2), 15% percent of whom (approximately 2.3 percent overall) had high-grade cancers. In another study, only 25-35 percent of men with PSA level between 4.1-9.9 ng/mL and who underwent a prostate biopsy had prostate cancer. Thus, there is no specific normal or abnormal PSA level, particularly since factors such as inflammation (e.g., prostatitis) and variation between laboratories can cause a PSA level fluctuations. In general, however, higher PSA levels correlate with higher probabilities of cancer.

The Gleason grading system is widely used in prostate cancer. It is determined by summing a primary (representing the majority of tumor) and secondary (assigned to the minority of the tumor) Gleason grade, each a number between 1 and 5. The sum of the two patterns is the Gleason score, which has prognostic significance. Patients with a Gleason score of ≤4 do well clinically, while patients with a score of 8-9 do poorly. A Gleason score of 6 typically is followed by "watchful waiting".

RNA Interference

Non-coding RNAi molecules regulate genes post-transcriptionally and can lead to gene silencing. Endogenous dsRNA initiates RNAi by activating the ribonuclease protein Dicer, which binds and cleaves double-stranded RNAs (dsRNAs) to produce double-stranded fragments of 20-25 base pairs with a 2-nucleotide overhang at the 3' end, known as siRNAs. These interfering RNAs (siRNAs) are integrated into an active RNA-induced silencing complex (RISC), while being separated into single "sense" and "antisense" strands. Within the RISC, the antisense strand then base-pairs to its target mRNA and induces cleavage of the mRNA, thereby preventing it from being used as a translation template. Synthetic siRNA can vary widely in their design, including the specific sequence along the mRNA, accessibility to Dicer and RISC, the length of each strand, optional symmetrical, asymmetrical, blunt, and loop structures, and chemical modifications of many types.

The delivery of RNAi to target tissue is a major challenge. Systemic injection of siRNA into the vascular system needs to overcome renal filtration and phagocytosis and degradation in the bloodstream, and needs to achieve targeting to the diseased site, transport across the vascular endothelial barrier, diffusion through the extracellular matrix, uptake into the cell, escape from the endosome, and unpackaging and releasing the siRNA to the cell RNAi machinery. Systemic delivery today is limited to a small number of target tissues, in particular to the liver.

Even direct injection of naked siRNA to topical targets (for example the eye, skin, mucus membranes, and localized tumors) and intranasal/intratracheal instillation of aerosolized siRNA into the lung is subject to rapid dose decline by diffusion and degradation and increased pressure (in some cases of injection). Repeated injections at a frequency of about one per week are often required.

Alshamsan et al. (*STAT3 Silencing in Dendritic Cells by siRNA Polyplexes Encapsulated in PLGA Nanoparticles for the Modulation of Anticancer Immune Response, Molecular Pharmaceutics* 7(5): 1643-1654, 2010) reported nanoparticles containing siRNA complexed with polyethylenimine (PEI). However, these devices exhibit fast drug release, typically on the order of one week, and are ineffective to carry high drug loads to a wide tissue area, for a sufficient treatment period.

US Patent Publication No. US2008/0124370 (Marx) describes reagents, methods and systems to treat inflammation and pain in a subject using small interfering RNA (siRNA) molecules targeted to either TNF-alpha, Il1, IL6 and other pro-inflammatory cytokines.

US Patent Publication No. US 2011/0195123 (Shemi) describes an implantable medical device eluting drug locally and for a prolonged period, treatment methods, and implantation methods. The device comprises a polymeric substrate and a drug, for example gene silencing drugs based on RNA interference (RNAi), including siRNA, shRNA, or antisense RNA/DNA, ribozyme and nucleoside analogs.

Thus, a continuing need exists for RNAi compositions to effectively treat prostate cancer.

SUMMARY

It has been discovered that prostate carcinoma can be treated by regional, prolonged release of an RNAi-based agent that targets prostate carcinoma-related proteins. Provided herein are systems and methods for treatment of prostate carcinoma. The systems and methods alternatively include manufacturing and implanting polymeric implant(s) loaded with agent, the combination of release parameters enabling treatment periods of various lengths, exploiting the RNAi machinery for specific silencing and RNAi for non-specific immune triggering, the shielding of the RNAi agent against degradation until it is released from the implant, the selected targets, and the release of naked, modified, complexed or conjugated types of siRNA. Such modifications can enable improved treatment efficiency by enhancing cellular uptake and/or spatial distribution, and can reduce toxicity levels.

BRIEF DESCRIPTION OF THE FIGURES

FIG. 2A: Short release periods (~1.5 month). NC=uncoated drug delivery device (DDD); C=coated DDD; Additive I=Mannitol ("Add1", 5% and 10%); Additive II=Trehalose ("Add2", 1%, 5% and 10%); "Conjugated"=cholesterol-conjugated (with Mannitol 10%). All samples were non-coated, except for the one indicated as coated. FIG. 2B: Longer release periods ~(3-6 months).

FIG. 9A shows the Argonaut (Ago) cleavage site on an siRNA with overhangs and exemplary sites for modifications. FIG. 9B shows the Ago cleavage site on a blunt-ended siRNA and exemplary sites for modifications.

SEQUENCE LISTING

Figure 1:
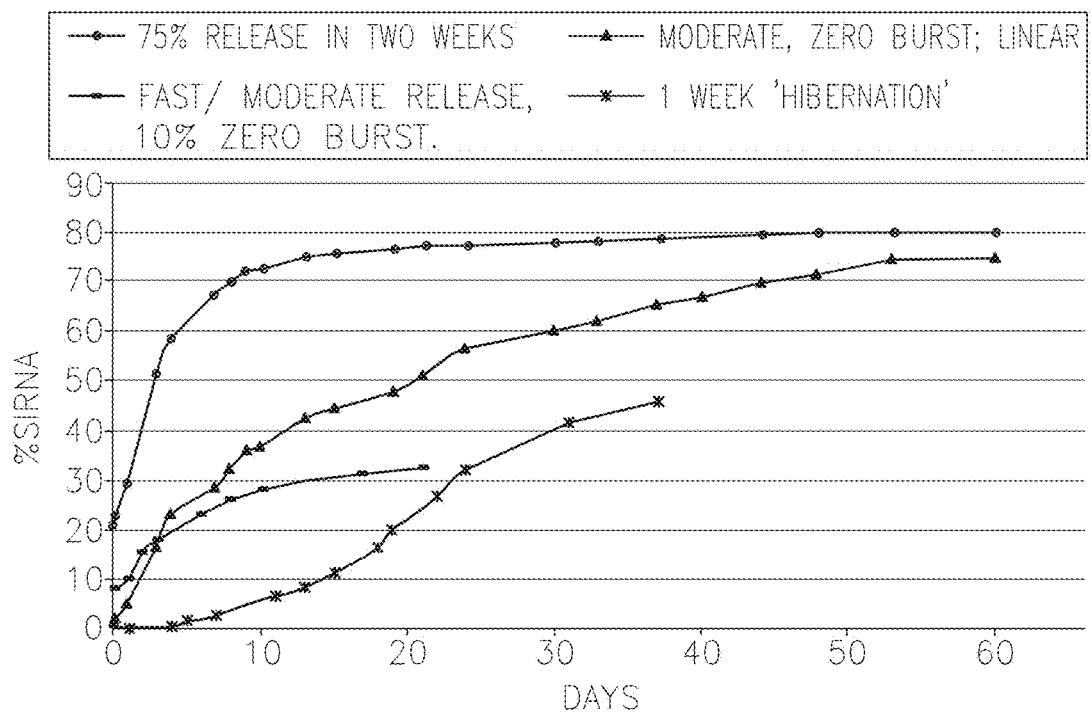
FIG. 1: shows exemplary time-release curves of siRNA, as measured in PBS, pH~7.

The nucleic and/or amino acid sequences listed in the accompanying sequence listing are shown using standard letter abbreviations for nucleotide bases, and three letter code for amino acids, as defined in United States of America Title 37 Code of Federal Regulations 1.822. In cases where only one strand of each nucleic acid sequence is shown, the complementary strand is understood as included by any reference to the displayed strand. The Sequence Listing is submitted as an ASCII text file named "2142_1_3001_seqlist", originally created Nov. 11, 2012, about 34 KB, which is incorporated by reference herein. In the accompanying sequence listing:

SEQ ID NOs 1-33 are the target sequences set forth in Table 2.

The even-numbered sequences from SEQ ID Nos: 34-102 are the sense siRNA sequences set forth in Table 2.

The odd-numbered sequences from SEQ ID Nos: 35-103 are the antisense siRNA sequences set forth in Table 2.

SEQ ID NOs 104-107 are exemplary sequences having 2'-OMe-modifications and dTdT tails.

SEQ ID NOs 108-109 are the sense and antisense strands, respectively of the siG12D utilized herein.

SEQ ID NOs 110-114 are exemplary sequences of cell-penetrating peptides.

DETAILED DESCRIPTION

Described herein is a millimeter-scale DDD comprising: (a) a biodegradable matrix; and (b) an RNA interfering (RNAi) agent that targets a prostate-carcinoma-related target gene. Typically, the biodegradable matrix is a biodegradable polymeric matrix, meaning that it comprises a polymer. In some embodiments, the RNAi agent is incorporated within the biodegradable matrix. In other embodiments, the RNAi agent is dispersed within the biodegradable matrix.

The term "RNAi agent", in certain embodiments, may refer to a nucleotide molecule that decreases or "downregulates" the level of an RNA target in a cell in a sequence-specific manner. In other embodiments, the RNA target is a messenger RNA.

In particular embodiments, RNAi nucleotides are short (or small) interfering RNA (siRNA), short hairpin RNA (shRNA), and microRNA. Other embodiments include longer polynucleotide molecules that are processed intracellularly to yield siRNA. Such molecules include DsiRNA, which are cleaved by the RNase III class endoribonuclease dicer into 21-23 base duplexes having a 2-base 3'-overhang; UsiRNAs, which are duplex siRNAs that are modified with non-nucleotide acyclic monomers, termed unlocked nucleobase analogs (UNA), in which the bond between two adjacent carbon atoms of ribose is removed—these may be designed to enter the RNAi (RNA inhibitory) pathway via Dicer enzyme or directly into RISC; self-delivering RNA (sdRNA) such as rxRNA® of RXi Therapeutics, which has a single-stranded phosphorothioate region, a short duplex region, and contains a variety of nuclease-stabilizing and lipophilic chemical modifications; aptamers, triple-helix antisense nucleotides, DNAzymes; and agents inhibiting the pre-mRNA maturation step of polyA tail addition such as the U1 adaptor (Integrated DNA Technologies (IDT) Inc). The U1 adaptor consists of two parts, a target-gene binding domain and a U'1 domain that attracts and inhibits the cellular splicing apparatus. By combining both capabilities in the same molecule, the U1 adaptor can inhibit the pre-mRNA maturation step of polyA tail addition.

Target Genes

"Prostate-cancer-related target gene" refers, as used herein, to a gene that is upregulated in prostate carcinoma cells (in all or a fraction of tumors, preferably at least 10% of tumors) relative to healthy (non-cancerous) prostate tissue. In other embodiments, the term refers to a gene that is upregulated in prostate carcinoma cells with metastatic potential relative to healthy somatic cells. In other embodiments, the term refers to a gene that is upregulated (whose expression is increased) in all or a fraction of prostate tumors relative to healthy somatic cells. Alternatively, the term may refer to a gene that is upregulated in all or a fraction of prostate tumors relative to non-embryonic somatic cells. In other embodiments, the target prostate cancer-related gene is expressed in all or a portion of prostate tumors and is undetectable in healthy tissue by standard methods such as gene expression array.

Non-limiting examples of preferred prostate-carcinoma-related genes are set forth in Table 1. In certain embodiments, the target is selected from Androgen Receptor, Pregnancy-associated plasma protein A (Pappalysin; PAPPA), Neurophilin and tolloid-like 2 (NETO2), Protein tyrosine phosphatase receptor α (PTPRA), BMI1 polycomb ring finger oncogene (BMI-1), Interleukin 6 signal transducer (IL6ST)/gp130, human Telomerase reverse transcriptase (hTERT), Bromodomain containing 4 (BRD4), ErbB3/HER3, PSCA prostate stem cell antigen (PSCA), Enhancer of zeste homolog 2 (EZH2), Transmembrane protease, serine 2 (TMPRSS2)/Ets Related Gene (ERG) gene fusion (TMPRSS2/ERG), Carbonic anhydrase XII (CA12), MEK4/MAP2K4, p63/KET, Transmembrane and coiled-coil protein 1 (TMCC1), TMCC2, TMCC3, Neurotrimin (NTM), Cluster of Differentiation 70 (CD70), Transmembrane protein 50B (Tmem50b), Claudin-11 (CLDN11), Neuroplastin NPTN, and CD44. Each target represents a separate embodiment.

In more specific embodiments, the target may be selected from the group consisting of Androgen Receptor, Pappalysin, NETO2, PTPRA, BMI-1, IL6ST/gp130, hTERT, BRD4, ErbB3/HER3, PSCA, and EZH2.

In other embodiments, the target may be selected from the group consisting of Androgen Receptor, Pappalysin, NETO2, PTPRA, BMI-1, IL6ST/gp130, BRD4, and EZH2.

In addition to the role of these prostate-carcinoma-related genes in prostate cancer, the role of such genes in more cancers has been intensively explored and in some cases demonstrated. Recently, Song et al (Cancer Sci 2010; 101: 1754-1760) found that BMI-1 plays an important role in the late progression of pancreatic cancer and may represent a novel therapeutic target for the treatment of pancreatic cancer.

Reference to a particular gene or protein herein includes, in some embodiments, all isoforms of the gene or protein.

In certain, more specific embodiments, the target is associated with prostate carcinoma stem cells. Non-limiting examples of prostate carcinoma stem cell targets are CA12, p63, Pappalysin, NETO2, Protein tyrosine phosphatase receptor α, TMCC1, TMCC2, TMCC3, Neurotrimin, CD70, Tmem50b, Claudin-11, and Neuroplastin NPTN. In other embodiments, the target is another prostate carcinoma target. In other embodiments, the target is another stem cell-specific target.

TABLE 1

Exemplary RNAi Targets:

| Name | Synonyms/ GenBank Gene ID No. | Exemplary GenBank Accession #'s | Remarks |
|---|---|---|---|
| Androgen Receptor | KD; AIS; TFM; DHTR; SBMA; HYSP1; NR3C4; SMAX1; HUMARA Gene ID #: 367 | NM_000044.3 NM_001011645.2 NM_000044.2 M20132.1 FJ235918 NM_001011645.1 | Expressed in 100% of prostate cancer lesions |
| Pappalysin | PAPPA pregnancy-associated plasma protein A Gene ID #: 5069. | NM_002581.3 | |
| NETO2 | Neurophilin (NRP) and tolloid (TLL)-like 2; BTCL2; NEOT2. Gene ID #: 81831. | NM_001081324.1 NM_001201477.1 (variant 2) NM_018092.4 (variant 1) | Transcript variants 1 and/or 2 can be targeted |
| Protein tyrosine phosphatase receptor α (PTPRA) | LRP; HLPR; PTPA; HEPTP; HPTPA; RPTPA; PTPRL2; HPTPalpha; R-PTP-alpha. Gene ID #: 5786. | NM_080840.2 NM_001163688.1 | |
| BMI-1 | BMI1 polycomb ring finger oncogene, Gene ID # 648 | NC_000010.10 | |

TABLE 1-continued

Exemplary RNAi Targets:

| Name | Synonyms/ GenBank Gene ID No. | Exemplary GenBank Accession #'s | Remarks |
|---|---|---|---|
| gp130 | IL6ST interleukin 6 signal transducer; CD130; CDW130; IL-6RB. Gene ID # 3572. | NM_001190981.1 NM_175767.2 NM_002184.3 | |
| hTERT | TERT telomerase reverse transcriptase Gene ID # 7015 | NM_001193376 NM_198253.2 | |
| BRD4 | BRD4 bromodomain containing 4; CAP; MCAP; HUNK1; HUNKI. Gene ID # 23476. | NM_014299.2 NM_058243.2 | |
| ErbB3 | HER3; LCCS2; ErbB-3; c-erbB3; erbB3-S; MDA-BF-1 Gene ID # 2065 | NM_001005915.1 NM_001982.3 NP_001973 | |
| PSCA | PSCA prostate stem cell antigen; PRO232 Gene ID # 8000 | NM_005672.4 NP_005663 | |
| EZH2 | Enhancer of zeste homolog 2; ENX1; EZH1; KMT6; WVS2; ENX-1; KMT6A. Gene ID # 2146 | NM_004456.4 NM_152998.2 NM_001203247.1 NM_001203248.1 NM_001203249.1 | |
| CD44 | | NM_001202557.1 NM_001202556.1 NM_001202555.1 NM_001001392.1 NM_001001391.1 NM_001001390.1 NM_001001389.1 NM_000610.3 | |

Additional Targets

TMPRSS2/ERG fusion gene is a fusion of ERG v-ets erythroblastosis virus E26 oncogene homolog (also known as erg-3; Gene ID#: 2078) to TMPRSS2 transmembrane protease, serine 2 (also known as PP9284 or PRSS10; Gene ID#: 7113). It is expressed in 15-80% of prostate cancer lesions.

CA12 Carbonic anhydrase XII (also known as CAXII or HsT18816; Gene ID #: 771) is a transmembrane and extracellular enzyme involved in the regulation of microenvironment acidity and tumor malignancy. CA XII has a central role in hypoxia and tumor acidosis, invasion and metastasis. Representative GenBank sequence: NM_001218.3.

MEK4 (also known as MAP2K4; JNKK; MEK4; MKK4; SEK1; JNKK1; SERK1; MAPKK4; PRKMK4; SAPKK1; and SAPKK-1; Gene ID #: 6416) regulates prostate cancer cell invasion/metastasis. See US 2009/0124569. Representative GenBank sequence: NM_003010.2.

p63 (also known as KET, p51A/B, CUSP, p40, and p73L; Gene ID #: 8626) is a transcription factor and homologue of p53. Representative GenBank sequences: NM_001114978.1, NM_001114979.1, NM_001114980.1, NM_001114981.1, NM_001114982.1, and NM_003722.4.

Transmembrane and coiled-coil proteins (TMCCs) are a group of putative proteins that contain a coiled-coil domain and two transmembrane domains. Both transmembrane domains are located in the C-terminal region (571-653a.a.). There are three family members in humans, which share high sequence homology, namely TMCC1, TMCC2, and TMCC3 (GenBank Gene ID #'s 23023, 9911, and 57458, respectively).

Neurotrimin is a glycosylphosphatidylinositol (GPI)-anchored cell adhesion molecule expressed on neuronal populations (GenBank Gene ID #50863).

CD70, a member of the tumour necrosis factor (TNF) superfamily, is a type II integral membrane protein and the ligand for CD27 (GenBank Gene ID #970).

Tmem50b (GenBank Gene ID #757) is one of two genes in the transmembrane 50 group.

Claudin-11, also known as oligodendrocyte-specific protein, was first identified to be specifically expressed in the tight junction (TJ) strands of oligodendrocytes in brain and in sertoli cells of rats and mice (GenBank Gene ID #5010).

Neuroplastin NPTN (previously known as stromal cell derived factor receptor I) is a cell adhesion molecule of the immunoglobulin (Ig) superfamily (GenBank Gene ID #27020).

CD44: CD44 is a multifunctional protein involved in cell adhesion and signaling. Studies have shown both tumor-promoting and tumor-inhibiting effects of CD44 in prostate cancer development and progression (Patrawala et al). Gene ID#960.

All isoforms of the proteins mentioned herein may be included. The mention of particular representative sequences is not intended to exclude isoforms not exemplified herein.

In other embodiments, the DDD comprises two or more separate RNAi agents. In other embodiments, 2 of the above-listed genes are targeted.

In other embodiments, the DDD further comprises an RNAi agent that targets a gene involved in vasculogenesis, angiogenesis and endothelial growth, and/or epidermal growth. In a more specific embodiment, the target is selected from VEGF (Vascular endothelial growth factor), Aurora B kinase (AURKB), and EGFR (epidermal growth factor receptor). In other embodiments, the angiogenesis target is targeted together with gene from Table 1 above. For example, a DDD may comprise a first RNAi agent that targets a gene selected from Androgen Receptor, Pappalysin, NETO2, PTPRA, BMI1, IL6ST/gp130, hTERT, BRD4, ErbB3/HER3, PSCA, EZH2, TMPRSS2/ERG, CA12, MEK4/MAP2K4, p63/KET, TMCC1, TMCC2, TMCC3, Neurotrimin, CD70, Tmem50b, Claudin-11, Neuroplastin NPTN, and CD44; and a second RNAi agent that targets a gene selected from VEGF, AURKB, and EGFR. In other embodiments, the DDD comprises a first RNAi agent that targets a gene selected from Androgen Receptor, Pappalysin, NETO2, PTPRA, BMI-1, IL6ST/gp130, hTERT, BRD4, ErbB3/HER3, PSCA, and EZH2; and a second RNAi agent that targets a gene selected from VEGF, AURKB, and EGFR. In still other embodiments, the DDD comprises a first RNAi agent that targets a gene selected from Androgen Receptor, Pappalysin, NETO2, PTPRA, BMI-1, IL6ST/gp130, BRD4, and EZH2; and a second RNAi agent that targets a gene selected from VEGF, AURKB, and EGFR.

In other embodiments, the angiogenesis target is targeted together with a prostate cancer stem cell target. In other embodiments, the DDD comprises a first RNAi agent that targets a gene selected from CA12, p63, Pappalysin, NETO2, Protein tyrosine phosphatase receptor α, TMCC1, TMCC2, TMCC3, Neurotrimin, CD70, Tmem50b, Claudin-11, and Neuroplastin NPTN; and a second RNAi agent that targets a gene selected from VEGF, AURKB, and EGFR.

In other embodiments, the angiogenesis gene is targeted together with two prostate cancer targets. In other embodiments, the two prostate cancer targets are targets listed in Table 1 above.

In other embodiments, the target of an siRNA present in a DDD of the methods and compositions described herein is one of the target sequences set forth in Table 2 (SEQ ID Nos: 1-33).

In other embodiments, the sense sequence of an siRNA present in a DDD of the methods and compositions described herein is one of the sense siRNA sequences set forth in Table 2 (even-numbered sequences from SEQ ID Nos: 34-102).

In other embodiments, the antisense sequence of an siRNA present in a DDD of the methods and compositions described herein is one of the antisense siRNA sequences set forth in Table 2 (odd-numbered sequences from SEQ ID Nos: 35-103).

TABLE 2

Exemplary target sequences and siRNA sequences.

| SEQ ID No: | Sequence name/ siRNA number | Target sequence/ Sense sequence/ Antisense sequence, 5'-3' | Position and GenBank Accession No. of targets; specificity; and other comments |
|---|---|---|---|
| 1 | siAR-1 | UGCCAGGGACCAUGUUUUG | NM_000044.3: 2741; |
| 34 | 201 | UGCCAGGGACCAUGUUUUGdTdT | NM_001011645.2: 192 |
| 35 | | CAAAACAUGGUCCCUGGCAdTdT | |
| 2 | siAR-2 | CGGAAAUGUUAUGAAGCAG | NM_000044.3: 2967 |
| 36 | 202 | CGGAAAUGUUAUGAAGCAGdTdT | NM_001011645.2: 418 |
| 37 | | CUGCUUCAUAACAUUUCCGdTdT | |
| 3 | siAR-3 | GCUGAAGAAACUUGGUAAU | NM_000044.3: 3626 |
| 38 | 203 | GCUGAAGAAACUUGGUAAUdTdT | NM_001011645.2: 1077 |
| 39 | | AUUACCAAGUUUCUUCAGCdTdT | |
| 4 | siAR-4 | UGAUUUAUACUUCUCUGUU | NM_000044.3: 3026 |
| 40 | 204 | UGAUUUAUACUUCUCUGUUdTdT | NM_001011645.2: 477 |
| 41 | | AACAGAGAAGUAUAAAUCAdTdT | |
| 5 | siBMI1-1 | UGAUUUAUACUUCUCUGUU | siBMI-1-1 start 2016, Hs |
| 42 | 205 | UGAUUUAUACUUCUCUGUUdTdT | and Mm |
| 43 | | AACAGAGAAGUAUAAAUCAdTdT | |
| 6 | siBMI1-2 | AUGAAUGGAACCAGCAACA | siBMI-1-2, start 1383, Hs |
| 44 | 206 | AUGAAUGGAACCAGCAACAdTdT | and Mm |
| 45 | | UGUUGCUGGUUCCAUUCAUdTdT | |
| 7 | siCDC44-1 | CUGAGCAUCGGAUUUGAGACUG | siCD44-1 (starts at 641, all 8 Hs variants, targets Hs only) |
| 46 | | CUGAGCAUCGGAUUUGAGAdTdT | |
| 47 | 207 | UCUCAAAUCCGAUGCUCAGdTdT | |
| 8 | siCDC44-2 | GGCGCAGAUCGAUUUGAAU | pos. 2003, Hs only, v-1 (NM_198253.2) and v-2 (NM_001193376.1) |
| 48 | | GGCGCAGAUCGAUUUGAAUdTdT | |
| 49 | 208 | UGAGACGCUCGGCCCUCUUdTdT | |
| 9 | si-hTERT-1 | AAGAGGGCCGAGCGUCUCA | siCD44-2 (starts at 491, all 8 Hs variants, targets Hs only) |
| 50 | | AAGAGGGCCGAGCGUCUCAdTdT | |
| 51 | 209 | AUUCAAAUCGAUCUGCGCCdTdT | |
| 10 | si-hTERT-2 | GAACGUUCCGCAGAGAAAA | starts at 1986, Hs only v-1 (NM_198253.2) and v-2 (NM_001193376.1) |
| 52 | | GAACGUUCCGCAGAGAAAAdTdT | |
| 53 | 210 | UUUUCUCUGCGGAACGUUCdTdT | |
| 11 | si-hTERT-3 | GCACUUCCUCUACUCCUCA | starts at 1045, Hs only |
| 54 | | GCACUUCCUCUACUCCUCAdTdT | |
| 55 | 211 | UGAGGAGUAGAGGAAGUGCdTdT | |

TABLE 2-continued

Exemplary target sequences and siRNA sequences.

| SEQ ID No: | Sequence name/ siRNA number | Target sequence/ Sense sequence/ Antisense sequence, 5'-3' | Position and GenBank Accession No. of targets; specificity; and other comments |
|---|---|---|---|
| 12<br>56<br>57 | si-hTERT-4<br>212 | CACCAAGAAGUUCAUCUCC<br>CACCAAGAAGUUCAUCUCCdTdT<br>GGAGAUGAACUUCUUGGUGdTdT | starts at 1528, Hs only |
| 13<br>58<br>59 | si-hTERT-5<br>213 | CAUCGCCAGCAUCAUCAAA<br>CAUCGCCAGCAUCAUCAAAdTdT<br>UUUGAUGAUGCUGGCGAUGdTdT | starts at 2242, Hs only |
| 14<br>60<br>61 | siNETO2-1<br>214 | GACUCAUAUCCACCAAACA<br>GACUCAUAUCCACCAAACAdTdT<br>UGUUUGGUGGAUAUGAGUCdTdT | in open mRNA area: starting at 603nt in v 1&2, NM_001201477.1 (v2) and NM_018092.4 (v1) |
| 15<br>62<br>63 | siNETO2-2<br>215 | CAGGGAGAUUCAUGUGGAU<br>CAGGGAGAUUCAUGUGGAUdTdT<br>AUCCACAUGAAUCUCCCUGdTdT | starting at 811nt in both variants, NM_001201477.1 (v2) and NM_018092.4 (v1) |
| 16<br>64<br>65 | siNETO2-3<br>216 | GUCUUGGUCCUUCUCAUUA<br>GUCUUGGUCCUUCUCAUUAdTdT<br>UAAUGAGAAGGACCAAGACdTdT | starting at 1464 at v2 and 1485 at v1 |
| 3<br>66<br>67 | siAR-3-O-Me<br>217 | GCUGAAGAAACUUGGUAAU<br>GCoUGAAGAAACUoUGGoUAAU<br>AUoUACoCAAGUUUCUUoCAGC | Modified siAR-1. |
| 14<br>68<br>69 | siNETO2-1-O-Me<br>218 | GACUCAUAUCCACCAAACA<br>GACUoCAoUAUCoCACCoCAAAoCA<br>oUGUUoUGGoUGGAUAoUGAGUC | Modified siNETO2-1 |
| 17<br>70<br>71 | gp130<br>219 | GGCAUACCUUAAACAAGCU<br>GGCAUACCUUAAACAAGCUdTdT<br>AGCUUGUUUAAGGUAUGCCdTdT | targets all 3 variants: NM_001190981.1 (v3) at 1663, NM_175767.2 (v2) at 1763, NM_002184.3 (v1) at 1846 |
| 18<br>72<br>73 | PTPRA-1<br>220 | GACGACAAUAAGCUCUUCA<br>GACGACAAUAAGCUCUUCAdTdT<br>UGAAGAGCUUAUUGUCGUCdTdT | targets 3 Hs variants and Mm, starts at 1072 at v2 NM_080840.2 |
| 19<br>74<br>75 | PTPRA-2<br>221 | CCUUAUGACCACUCUAGAG<br>CCUUAUGACCACUCUAGAGdTdT<br>CUCUAGAGUGGUCAUAAGGdTdT | targets 3 Hs variants, starts at 1192 at v2 NM_080840.2 |
| 20<br>76<br>77 | PTPRA-3<br>222 | GAUGAGACACCAAUUAUUG<br>GAUGAGACACCAAUUAUUGdTdT<br>CAAUAAUUGGUGUCUCAUCdTdT | targets 3 Hs variants and Mm, starts at 808 at v2 NM_080840.2 |
| 21<br>78<br>79 | PTPRA-4<br>223 | GCCAAAACUUCAAAUCCAA<br>GCCAAAACUUCAAAUCCAAdTdT<br>UUGGAUUUGAAGUUUUGGCdTdT | targets 3 Hs variants, starts at 532 at v2 NM_080840.2 |
| 22<br>80<br>81 | PTPRA-5<br>224 | CCACAAGAACAGCAAGCAC<br>CCACAAGAACAGCAAGCACdTdT<br>GUGCUUGCUGUUCUUGTGGdTdT | targets 3 Hs variants, starts at 654 at v2 NM_080840.2 |
| 23<br>82<br>83 | PAPPA-1<br>225 | CGACGACAUGAAUAAGAUC<br>CGACGACAUGAAUAAGAUCdTdT<br>GAUCUUAUUCAUGUCGUCGdTdT | targets Hs and Mm, starts at nt 3261 at NM_002581.3 |
| 24<br>84<br>85 | PAPPA-2<br>226 | CCAUCAGCUACCCAUAUUC<br>CCAUCAGCUACCCAUAUUCdTdT<br>GAAUAUGGGUAGCUGAUGGdTdT | targets Hs , starts at nt 3593 at NM_002581.3 |
| 25<br>86<br>87 | PAPPA-3<br>227 | GGAAGGCAACCAGCUGUUA<br>GGAAGGCAACCAGCUGUUAdTdT<br>UAACAGCUGGUUGCCUUCCdTdT | targets Hs and Mm, starts at nt 100 at NM_002581.3 |
| 26<br>88<br>89 | siErbB3-1<br>228 | GCTGAGAACCAATACCAGA<br>GCTGAGAACCAATACCAGAdTdT<br>TCTGGTATTGGTTCTCAGCdTdT | both variants, NM_001982.3 and NM_001005915.1, 317-335 in NM_001005915.1 |

TABLE 2-continued

Exemplary target sequences and siRNA sequences.

| SEQ ID No: | Sequence name/ siRNA number | Target sequence/ Sense sequence/ Antisense sequence, 5'-3' | Position and GenBank Accession No. of targets; specificity; and other comments |
|---|---|---|---|
| 27 90 91 | siErbB3-2 229 | CAACUCUCAGGCAGUGUGU<br>CAACUCUCAGGCAGUGUGUdTdT<br>ACACACUGCCUGAGAGUUGdTdT | both variants, 262-280 in NM_001005915.1 |
| 28 92 93 | siPSCA-1 230 | CACGAAGGCUGUGCUGCUU<br>CACGAAGGCUGUGCUGCUUdTdT<br>AAGCAGCACAGCCUUCGUGdTdT | Targets NM_005672.4 at 56-74 |
| 29 94 95 | siPSCA-2 231 | CGUGCUGUGACACCGACUU<br>CGUGCUGUGACACCGACUUdTdT<br>AAGUCGGUGUCACAGCACGdTdT | NM_005672.4 at 310-328 |
| 30 96 97 | siBrd4-1 232 | CCAACGCAGCCAGCACCAA<br>CCAACGCAGCCAGCACCAAdTdT<br>UUGGUGCUGGCUGCGUUGGdTdT | both variants: NM_014299.2 and NM_058243.2 |
| 31 98 99 | siBrd4-2 233 | CUGGAAUGCUCAGGAAUGU<br>CUGGAAUGCUCAGGAAUGUdTdT<br>ACAUUCCUGAGCAUUCCAGdTdT | targets both variants |
| 32 100 101 | siEZH2-1 234 | CCUGACCUCUGUCUUACUU<br>CCUGACCUCUGUCUUACUUdTdT<br>AAGUAAGACAGAGGUCAGGdTdT | all 5 variants: NM_004456.4 (v1), NM_152998.2 (v2), NM_001203247.1 (v3), NM_001203248.1 (v4), NM_001203249.1 (v5); 1952-1970 in v1 |
| 33 102 103 | siEZH2-2 235 | CUGGGAAGAAAUCUGAGAA<br>CUGGGAAGAAAUCUGAGAAdTdT<br>UUCUCAGAUUUCUUCCCAGdTdT | all 5 variants: 204-222 in v1 |

Modifications of Specific Sequences

In other embodiments, the following 4 sequence criteria are used to design additional siRNA molecules:
(1) AU richness in the 5'-terminal, 7-bp-long region of the antisense strand;
(2) G/C at the 5' end of the sense strand; and
(3) the absence of any long GC stretch of >9 bp in length.
(4) a G/C content ranging from 36% to 52%.

In certain embodiments, an RNAi agent that is used is between 25-30 nt, inclusive, in length. More specifically, the length may be 25-27 nt. In other embodiments, the length is 19-25-nt. In other embodiments, the length is 19 nt. In other embodiments, the sense strand and/or the antisense strand further comprises a 1-6-nt 3'-overhang. In other embodiments, a two-base 3' overhang is present. In more specific embodiments, the sense strand and the antisense strand each further comprises a 2-nt 3'-overhang.

siRNA structure determinants: In one embodiment, the A-form helix of the guide strand-mRNA duplex is preferred. A 25-30-nt asymmetric dsRNAs with a 5' blunt end and a 2-nt 3' overhang on the other end is also preferred. In certain embodiments, a blunt structure at the 3' end is present, followed by a 5' overhang.

Loops, if present, may be preferably on the 3' end of the sense strand, or also may be on the 5' end of the sense strand. The loop may contain nucleotides optionally in combination with non-nucleotide residues.

In other embodiments, an siRNA used in the described methods and compositions has a 19+2 overhang design, namely sense and anti-sense of 19 base-paired nucleotides and two unpaired nucleotides at the 3' end of each of the strands. In certain embodiments, as exemplified herein, the overhangs are each dTdT (2 deoxythymidine residues). Non-limiting examples of siRNA molecules with dTdT tails are shown in Table 2.

In other embodiments, one or both strands of an siRNA described herein is modified by 2'-OMe, 2'-F, or another modification. In some embodiments, the positions identified below as "o" may be modified with 2'-OMe:

```
AR siRNA (#217):
                                       (SEQ ID No: 66)
Sense:    5' GCoUGAAGAAACUoUGGoUAAU (SEQ ID No: 67)
Antisense: 3' AUoUACoCAAGUUUCUUoCAGC siNETO2 (#218):
                                       (SEQ ID No: 68)
Sense:    5' GACUoCAoUAUCoCACoCAAAoCA (SEQ ID No: 69)
Antisense: 5' oUGUUoUGGoUGGAUAoUGAGUC
```

2'-OMe-modified oligonucleotides may be used with or, in other embodiments without, overhangs at the 3' end of each of the strands. In certain embodiments, the overhangs each consist of two unpaired nucleotides. In more specific embodiments, as exemplified herein, the overhangs are each dTdT (2 deoxythymidine residues). Non-limiting examples of siRNA molecules with 2'-OMe-modifications and dTdT tails are shown below.

AR siRNA + tail:
(SEQ ID No: 104)
Sense: 5' GC<u>oU</u>GAAGAAACU<u>oU</u>GG<u>oU</u>AAUdTdT (SEQ ID No: 105)
Antisense: 3' AU<u>oU</u>AC<u>oC</u>AAGUUUCUU<u>oC</u>AGCdTdT siNETO2 + tail:
(SEQ ID No: 106)
Sense: 5' GACU<u>oC</u>A<u>oU</u>AUC<u>oC</u>AC<u>oC</u>AAA<u>oC</u>AdTdT (SEQ ID No: 107)
Antisense: 5' <u>oU</u>GUU<u>oU</u>GG<u>oU</u>GGAUA<u>oU</u>GAGUCdTdT.

Chemical Modifications

In other embodiments, an RNAi agent used in the described methods and compositions may be chemically modified. In another embodiment, the modification is a backbone or linkage modification. In another embodiment, the modification is a nucleoside base modification. In another embodiment, the modification is a sugar modification. In more specific embodiments, the modification is selected from the modifications appearing in Table 2 hereinbelow. In more specific embodiments, the modification is selected from a 2'-O-methyl (2'-OMe), 2'-O-(2-methoxyethyl) (MOE) and 2'-fluorine modification. In still more specific embodiments, the modification is a 2'-O-methyl (2'-OMe) modification. In other embodiments, the modification is selected from a locked nucleic acid (LNA) and/or peptide nucleic acid (PNA) backbone.

Figure 9A:
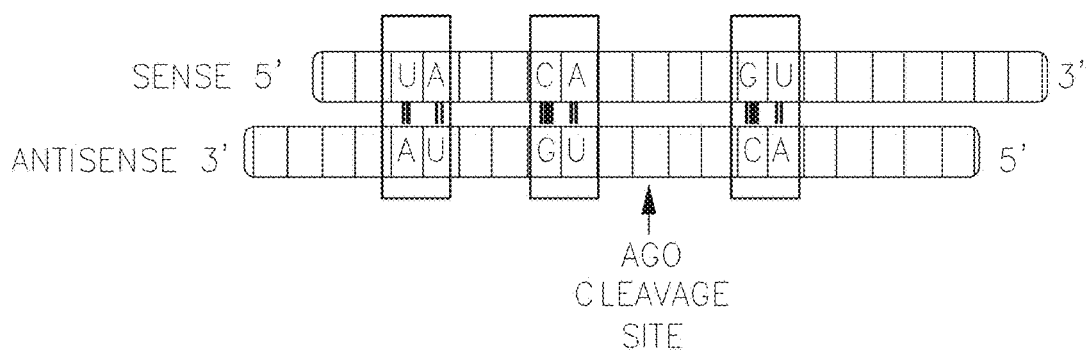
FIGS. 9A-B.
Figure 9B:
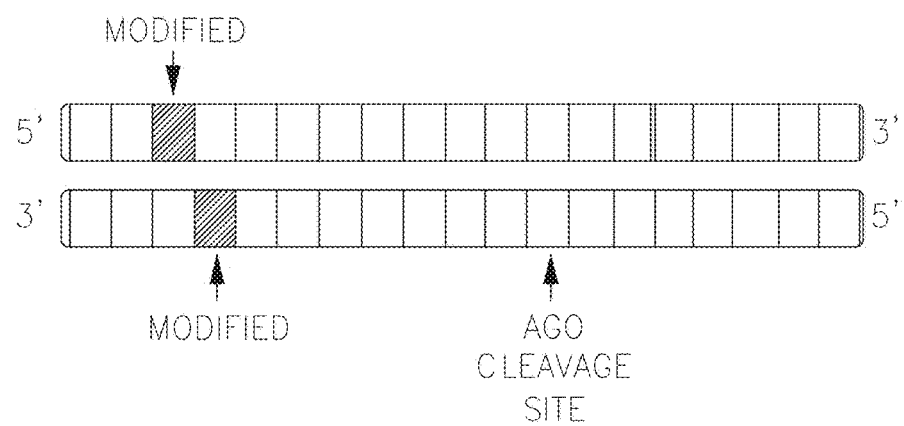

In some embodiments, siRNA modifications are designed based on the following guidelines:
1. Cluster modifications around endonuclease cleavage sites: 5'-UA, 5'-CA, 5'-UG
2. When choosing modification sites use the following guiding rules:
   a. Fewer modifications on the antisense strand compared to the sense strand.
   b. Avoid modifications on the Argonaut (Ago) cleavage site (the 10nth nucleotide on antisense strand; FIGS. 9A-B).
   c. As modification increases duplex stability, therefore make fewer modifications on the 3' end of the sense strand or the 5' end of antisense strand.
3. Order modifications in diagonal 5' to 5'.
4. Use of blunt ends instead of overhangs lower exonuclease activity.

TABLE 3

Selected chemical modifications.

| Modification | Position of the substitution |
|---|---|
| Sugar modifications | |
| dNTPs-dTdT | 3'-overhangs of sense and anti-sense strands |
| dNTPs-dNPs | Any number of residues in the sense strand; 0-4 residues at the 5' end of the antisense strand |
| 2'-O-methyl (2'OMe) rNPs | Any number of residues in the sense and antisense strands |
| 2'-fluoro (2'-F) rNPs | Any number of pyrimidine residues in the sense and antisense strands |
| combined use of 2'OMe and 2'-F | Any number of pyrimidine residues in the sense and antisense strands to 2'-F; and any number of purine residues in the sense and antisense strands to 2'-OMe. |
| 2'-O-(2-methoxyethyl) (MOE) rNPs | Any number of pyrimidine residues in the sense and antisense strands |
| 2'-fluoro-β-D (FANA) rNPs | Any number of pyrimidine residues in the sense strand |
| Locked nucleic acids (LNA) | from none till 4 last ribonucleotides at the 3' end of the sense strand; and 3' overhangs of the antisense strand |
| combined use of DNA and 2'-F | substitution of any number of pyrimidine (T and C) ribonucleotides to 2'-F ribonucleotides and any number of purines (A and G) to deoxyribonucleotides in sense and antisense strands |
| phosphate linkage modifications-phosphorotioate (PS) | |
| phosphodiester | substitution of any number of ribonucleotides in sense and antisense strands |
| phosphothioate (PS) | substitution of any number of ribonucleotides in sense and antisense strands |
| boranophosphate DNA or RNA | substitution of any number of ribonucleotides in sense and antisense strands |
| amide-linked | substitution of any number of ribonucleotides in sense and antisense strands |
| phosphoramidate | substitution of any number of ribonucleotides in sense and antisense strands |
| methylphosphonate | substitution of any number of ribonucleotides in sense and antisense strands |
| 2',5'-linked DNA or RNA | substitution of any number of ribonucleotides in sense strand |
| Base modifications | |
| 5-bromouracil (5-Br-Ura) | substitution of any number of ribouraciles in sense and antisense strands |
| 5-iodouracil (5-I-Ura) | substitution of any number of ribouraciles in sense and antisense strands |
| dihydrouracil | substitution of any number of ribouraciles in sense and antisense strands |
| 2-thiouracil | substitution of any number of ribouraciles in sense and antisense strands |
| 4-thiouracil | substitution of any number of ribouraciles in sense and antisense strands |
| pseudouracil | substitution of any number of ribouraciles in sense and antisense strands |
| diaminopurine | substitution of any number of adenines in both sense and antisense |
| difluorotoluene | substitution of any number of adenines in both sense and antisense |
| peptide nucleic acids (PNAs) (2-aminoethylglycine) | substitution of any number of ribonucleotides in sense and antisense strands |
| modifications to the overhangs and termini | |
| 2-nt-3'-DNA overhang | 3' end of sense and antisense strands |
| 2-nt-3'-RNA overhang | 3' end of sense and antisense strands |
| blunt-ended duplexes | 3' end of sense and antisense strands |
| chemical conjugation | |
| cholesterol | covalently attached to sense strand |
| vitamin-E (α-tocopherol) | covalently attached to sense strand |

In other embodiments, the chemical modification is a modification described in paragraphs 0040-0050 of US Patent Application Pub. No. 2011/0195123, the contents of which are incorporated herein by reference.

In other embodiments, the chemical modification is a modification to the overhang(s) and/or termini, or to the duplex architecture, as described in paragraphs 0061 and 0062, respectively, of US Patent Application Pub. No. 2011/0195123.

In other embodiments, an RNAi agent used in the described methods and compositions may be conjugated to a molecule. In more specific embodiments, a non-nucleotide molecule is used. In more specific embodiments, the molecule may be cholesterol, a cell penetrating peptide, or alpha-tocopherol-vitamin E. In certain embodiments, the cholesterol may be conjugated to the 3' end of the sense strand. In other embodiments, the cholesterol may be conjugated to the 5' end of the sense strand. In certain embodiments, in the case of a hairpin-shaped molecule, the cholesterol may be conjugated to the loop. In other embodiments, the non-nucleotide molecule is a molecule described in paragraphs 0051-0060 of US Patent Application Pub. No. 2011/0195123.

In certain embodiments, the RNAi agent is associated, either via covalent attachment or via non-covalent complexation, with a cell-penetrating peptide (CPP), also referred to as protein transduction domains (PTDs). A CPP is a peptide that has the ability to traverse the plasma membrane and facilitate the delivery of a molecular cargo to the cytoplasm. CPP's include HIV-1 Tat (NCBI Gene ID: 155871) or a fragment thereof comprising the sequence YGRKKRRQRRR (SEQ ID No: 110); pAntp (penetratin) and pIsl, which originate from the third helix of homeodomain proteins (Antennapedia (NCBI Gene ID: 40835; Terrone et al) and Isl-1 (NCBI Gene ID: 3670 and Magzoub et al), respectively); Transportan, a synthetic chimera of galanin and mastoparan (GWTLNSAGYLLGKINLKA-LAALAKKIL-amide [SEQ ID No: 111]; Pooga et al), MPG (GALFLGFLGAAGSTMGA [SEQ ID No: 112]); Pep-1 (KETWWETWWTEW SEQ ID No: 113]); and secondary amphipathic peptides based on aromatic tryptophan and arginine residues linked with lysine as spacer ("CADY"), which contain a short peptide sequence of 20 amino acids, with the sequence "Ac-GLWRALWRLLRSLWRLLWRA-cysteamide" (SEQ ID No: 114). CPP's are known to those skilled in the art and are described inter alia in Deshayes et al.

In other embodiments, an RNAi agent used in the described methods and compositions may be complexed with a cationic molecule, such as DOTAP (N-[1-(2,3-Dioleoyloxy)propyl]-N,N,N-trimethylammonium) DOPE (1,2-dioleoyl-sn-glycero-3-phosphatidylethanolamine), 1,2-dioleoyl-sn-glycero-3-phosphocholine (DOPC), 1,2-di-O-octadecenyl-3-trimethylammonium propane (DOTMA), spermine, PEI (polyethylenimine), a PEI-PLA polymer, or N-Acetylgalactosamine (GalNAc). In other embodiments, the non-nucleotide molecule is a molecule described in paragraphs 0051-0060 of US Patent Application Pub. No. 2011/0195123.

In other embodiments, an RNAi agent used in the described methods and compositions is a hairpin-shaped molecule. In another embodiment, an RNAi agent used in the described methods and compositions is a double-stranded molecule containing 2 separate strands. In another embodiment, the RNAi agent is selected from the group consisting of a small interfering RNA (siRNA), a short hairpin RNA (shRNA), a Dicer-substrate siRNAs (DsiRNAs), a microRNA, and a non-coding RNA.

Millimeter-Scale Implant/Matrix Drug Delivery Technology

The drug delivery device of the described methods and compositions may be a cylinder, a sphere, or any other shape suitable for an implant (i.e. that can be implanted in a subject). In certain embodiments, the device is a cylinder.

"Millimeter-scale", as used herein, refers to a device whose smallest diameter is a least 0.3 mm. In certain embodiments, each of the dimensions (diameter, in the case of a sphere or cylinder; and height and/or width or length, in the case of a cylinder, box-like structure, cube, or other shape with flat walls) is between 0.3-10 mm, inclusive. In other embodiments, each dimension is between 0.5-8 mm, inclusive. In still other embodiments, each dimension is between 0.8-5.2 mm, inclusive, between 1-4 mm, inclusive, between 1-3.5 mm, inclusive, between 1-3 mm, inclusive, or between 1-2.5 mm, inclusive.

In yet other embodiments, the device is a cylinder, having a diameter of 0.8 mm. In other preferred embodiments, the cylinder has a length of 5 mm. In other embodiments, the cylinder has a diameter of 0.8 mm and a length of 5 mm. In other embodiments, a DDD of the described methods and compositions has the diameter of an 18-gauge needle.

In yet other embodiments, the device is cylindrical, with an 0.83-mm diameter (~0.033") and a length of 5 mm.

In other embodiments, the volume of the device is between 0.1 mm$^3$ and 1000 mm$^3$, between 0.2 mm$^3$ and 500 mm$^3$, between 0.5 mm$^3$ and 300 mm$^3$, between 0.8 mm$^3$ and 250 mm$^3$, between 1 mm$^3$ and 200 mm$^3$, between 2 mm$^3$ and 150 mm$^3$, between 3 mm$^3$ and 100 mm$^3$, or between 5 mm$^3$ and 50 mm$^3$.

An exemplary embodiment of a DDD has a diameter of 0.8 mm and a length of 5 mm, containing 25% w/w siRNA, namely about 650 μg of siRNA. In other embodiments, the DDD's contain siRNA; PLGA 85:15; D-Mannitol, and sodium bicarbonate. In other experiments, the DDD's contain siRNA, PLGA, trehalose, and sodium bicarbonate. In more particular embodiments, the molecular weight of the PLGA is between 5-15 kDa, inclusive.

In other embodiments, the w/w agent:polymer load ratio above 1:100. In more preferred embodiments, the load is above 1:20. In more preferred embodiments, the load is above 1:9. In more preferred embodiments, the load is above 1:3

In other embodiments, the device is a DDD that is described in US Patent Application Pub. No. 2011/0195123.

The DDD is designed in some embodiments to preferably employ degradable polymers, wherein the release mechanism includes both bulk erosion and diffusion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). The term "constant" refers to a diffusion rate that is preferably maintained above the lower threshold of therapeutic effectiveness, but which may still optionally feature an initial burst and/or fluctuate, for example increasing and decreasing to a certain degree. In other embodiments, there is an initial burst of less than 10% of the total amount of drug, which may be considered negligible. In other embodiments, there is an initial burst of about 20% of the total amount of drug. In other embodiments, the design enables initial a strong burst of 30% or more of the total amount of drug. The diffusion rate is preferably so maintained for a prolonged period, and it can be considered constant to a certain level to optimize the therapeutically effective period, for example the effective silencing period. These embodiments are described in US Patent Application Pub. No. 2011/0195123.

Suitable Release Profiles

In preferred embodiments, a device of the described methods and compositions is designed to release the active agent in a controlled fashion. It will be apparent to those of skill in the art, in light of the knowledge in the art taken together with the information provided herein, that the PLA:PGA ratio, composition and additives, and/or the molecular weight (MW) of the polymer, and controlling the surface-to-volume ratio of the implant may be adjusted to achieve a particular release profile. For example, deviating the PLA:PGA ratio from 50:50, or increasing the MW, or reducing surface-to-volume ratio can increase the release time.

In other embodiments, the DDD of the described methods and compositions is designed with a particular release profile. One relevant parameter is the time point at which 95% of the active agent has been released. In some embodiments, the DDD releases 95% of the active agent in vivo, for example in a human prostate, over a time period between 3-24 months inclusive, for example 3, 4, 5, 6, 8, 10, 12, 14, 16, 18, 20, 22, or 24 months. In other embodiments, the time point of release of 95% of the active agent is between 3-12 months inclusive, between 2-24 months inclusive, between 2-15 months inclusive, between 3-15 months inclusive, between 3-12 months inclusive, between 3-10 months inclusive, between 4-24 months inclusive. Another relevant parameter is the time point at which 90% of the active agent has been released; this may be any of the aforementioned time frames.

Another relevant parameter is the percent of active agent released at a given time point. For example, in some embodiments, 80-99% inclusive of the active agent is released at the 3-month timepoint. In other embodiments, 80-99% inclusive of the active agent is released at the 2-month timepoint or the 4-month, 6-month, 9-month, 12-month, or 24-month timepoint, each of which is considered a separate embodiment.

Alternatively or in addition, in some embodiments no more than 30-50% of the active agent of a DDD of the described methods and compositions is released during the first 3 weeks.

In other embodiments, a delayed-release DDD is utilized. "Delayed-release", as used herein, refers to DDD's that do not release more than 10% of their drug load within the first 2 months (discounting an initial burst of up to 20%, which sometimes occurs). In other embodiments, the DDD does not release more than 10% of its drug load within the first 3 months. The inventors have discovered that, in some embodiments, DDD's containing 1% trehalose exhibit delayed release. Trehalose has the additional advantage that, in some embodiments, it is effective at a concentration of only 1% (as opposed to 5-10% for mannitol, for example), thus allowing an increased drug load.

In other embodiments, the DDD is coated (by dipping, spraying, or any other method known to those skilled in the art) with a slowly-degraded polymer that contains no drug. Various embodiments of slowly-degraded polymers are described herein, each of which can be utilized to create a delayed-release DDD. In some embodiments, the coating comprises a linear-chain monosaccharide; a disaccharide; a cyclic monosaccharide, a cyclic disaccharide. In other embodiments, the coating comprising an additive selected from lactose, sucrose, dextran, and hydroxyethyl starch. In yet other embodiments, the coating comprises mannitol. Alternatively, the coating may comprise trehalose. In still other embodiments, the coating does not comprise a sugar.

In certain embodiments, less than 5% of the RNAi agent is released from the DDD over a time period of 1 month starting from implantation. In other embodiments, less than 10% of the RNAi agent is released from the DDD over a time period of 1 month starting from implantation.

In other embodiments, a delayed-release DDD is provided, comprising an siRNA against a target that is not a prostate-cancer-related target gene. In other embodiments, a therapeutic package is provided, comprising both (a) one or more delayed-release DDD and (b) one or more DDD that is not delayed-release. In some embodiments, the DDD comprise an siRNA against a prostate-cancer-related target gene. In other embodiments, siRNA is against a target that is not a prostate-cancer-related target gene.

Other exemplary release profiles are depicted in FIG. 1.

Suitable Biodegradable Matrices

In certain embodiments, the biodegradable matrix present in the drug delivery device comprises poly(lactic acid) (PLA). In other embodiments, the biodegradable matrix comprises poly(glycolic acid) (PGA). In other embodiments, the biodegradable matrix comprises both PLA and PGA (known as poly(lactic-co-glycolic acid) or PLGA).

Methods for making PLGA matrices that incorporate RNAi agents are well known in the art. Exemplary methods are described in described in US Patent Application Pub. No. 2011/0195123—for example in Examples 1.1 and 1.2 thereof.

In other embodiments, the PLA/PGA ratio of PLGA used in the methods and compositions is between 25:75 and 75:25. In other embodiments, the ratio is between 50:50 and 75:25, meaning that there is between 50-75% PLA and between 25-50% PGA in the biodegradable matrix (discounting substances other than polymer building blocks). In other embodiments, the PLA/PGA ratio is between 25:75 and 50:30, between 35:65 and 75:25, between 45:55 and 75:25, between 55:45 and 75:25, between 65:35 and 75:25, between 75:25 and 35:65, between 75:25 and 45:55, between 75:25 and 55:45, or between 75:25 and 65:25. In other embodiments, the PLA/PGA ratio is between 80:20 and 90:10, inclusive.

In other embodiments, the PLA/PGA ratio is larger than 75:25, between 75:25 and 85:15, or between 75:25 and 95:5. Alternatively, the ratio is smaller than 25:75, between 25:75 and 15:85, or between 25:75 and 5:95.

In other embodiments, the polymer comprises a polymer selected from the group consisting of poly(glycolide-co-lactide) (PLGA), polylactic acid (PLA) and polyglycolic acid (PGA) and polyethylene glycol (PEG). In other embodiments, the polymer comprises both PLA and PEG (poly(ethylene glycol)).

In other embodiments, tri-block PLA-PCL-PLA is used. PCL denotes poly-caprolactone.

In other embodiments, Poly(D,L-lactide) (DL-PLA), poly (D,L-glycolide), or poly(D,L-lactide-co-glycolide) is used, each of which is considered a separate embodiment.

Design of biodegradable controlled drug-delivery carriers containing PLA, PGA, PEG, and/or PCL to have a specified release profile is well-within the ability of those skilled in the art, and is described inter alia in Makadia and Siegel, *Poly Lactic-co-Glycolic Acid (PLGA) as Biodegradable Controlled Drug Delivery Carrier*, Polymers 2011, 3:1377-1397.

In another embodiment, the polymer is a polymer described in paragraphs 0076-0078 of US Patent Application Pub. No. 2011/0195123.

In some embodiments, a polymer used in the methods and compositions described herein has a molecular weight (MW) of greater than 5 kilodaltons (kDa). In other embodiments, the MW is greater than 50 kDa. In other embodiments, the MW is greater than 7 kDa, greater than 10 kDa, greater than 15 kDa, greater than 20 kDa, greater than 30 Da, greater than 70 kDa, greater than 100 kDa, greater than 150 kDa, or greater than 200 kDa. In other embodiments, the MW is between 5-100 kDa, inclusive, between 7-80 kDa, inclusive, between 10-60 kDa, inclusive, between 20-50 kDa, inclusive, or between 25-50 kDa, inclusive. As provided herein (Example 2), very slow release (approximately 6 months) can be achieved, PLGA of high PLA:PGA ratio, such as 90:10, and MW (molecular weight) higher than 50 KDa. A similar effect can be achieved by use of PLA.

In some embodiments, the polymer is L-PLA that has a molecular weight of greater than 5 kilodaltons (kDa). In other embodiments, the MW of the L-PLA is greater than 50 kDa. In other embodiments, the MW is greater than 7 kDa, greater than 10 kDa, greater than 15 kDa, greater than 20 kDa, greater than 30 Da, greater than 70 kDa, greater than 100 kDa, greater than 150 kDa, or greater than 200 kDa. In other embodiments, the MW of the L-PLA is between 5-100 kDa, inclusive, between 7-80 kDa, inclusive, between 10-60 kDa, inclusive, between 20-50 kDa, inclusive, or between 25-50 kDa, inclusive.

In some embodiments, the polymer is PLGA that has a molecular weight of greater than 5 kilodaltons (kDa). In other embodiments, the MW of the PLGA is greater than 50 kDa. In other embodiments, the MW is greater than 7 kDa, greater than 10 kDa, greater than 15 kDa, greater than 20 kDa, greater than 30 Da, greater than 70 kDa, greater than 100 kDa, greater than 150 kDa, or greater than 200 kDa. In other embodiments, the MW of the PLGA is between 5-100 kDa, inclusive, between 7-80 kDa, inclusive, between 10-60 kDa, inclusive, between 20-50 kDa, inclusive, or between 25-50 kDa, inclusive.

In some embodiments, the polymer has a PLA:PGA ratio of between 80:20 and 90:10, inclusive, for example 80:20, 82:18, 84:16, 86:14, 88:12, or 90:10, and a MW of greater than 50 KDa, for example greater than 50 Da, greater than 70 kDa, greater than 100 kDa, greater than 150 kDa, or greater than 200 kDa. In other embodiments, the polymer has a PLA:PGA ratio larger than 75:25, for example 76:24, 78:22, 80:20, 82:18, 84:16, 86:14, 88:12, 90:10, 92:8, 94:6, 96:4, or 98:2, and a MW of greater than 50 KDa. In yet other embodiments, the polymer has a PLA:PGA ratio smaller than 25:75, inclusive, for example 24:76, 22:78, 20:80, 18:82, 16:84, or 14:86, 12:88, 10:90, 8:92, 6:94, 4:96, or 2:98, and a MW of greater than 50 KDa. Each of the aforementioned PLA:PGA ratio may be freely combined with each MW value.

Additives

In other embodiments, the biodegradable matrix further comprises an additive for modulating hydrophilic-hydrophobic interactions; in other embodiments for enabling dispersion of the drug and eliminating aggregation; in other embodiments for preserving the drug in hot-temperature or cold-temperature storage conditions, for example 55° C. and −20° C., respectively, or significantly colder, in the case of lyophilization with liquid nitrogen; in other embodiments for facilitating creation of cavities in the implant that affect to drug diffusion from the matrix. Hydrophilic-hydrophobic interactions may cause aggregation of the active substance in cases of hydrophilic active substances, such as siRNA, incorporated within a hydrophobic polymer, resulting in aggregation during production or subsequently when the device is implanted into the body of a subject and it is subjected for example to hydrolysis. Non-limiting examples of such additives are open monosaccharides, for example mannitol; disaccharides such as trehalose; sorbitol; and other cyclic monosaccharides such as glucose, fructose, galactose and disaccharides such as sucrose. The above additives, when chiral, may be in the form of the D-enantiomer, the L-enantiomer, or a racemic mixture. Additional, non-limiting examples of such additives are lactose, sucrose, dextran, and hydroxyethyl starch.

In other embodiments, more than one additive is present.

In other embodiments, the biodegradable matrix further comprises an additive for protecting the drug against low pH after implantation. The microenvironment in the implant interior tends to be acidic. Unlike chemotherapy, pH should preferably be maintained above a threshold. While doxorubicin is stable in an acidic environment, with minimal hydrolytic degradation within a pH range of 3 to 6.5, RNAi drugs might degrade at pH <3. In more specific embodiments, this additive may be selected from bicarbonates and carbonates, for example sodium bicarbonate, sodium carbonate, and magnesium hydroxide.

In other embodiments, the biodegradable matrix further comprises a small-molecule therapeutic agent against prostate carcinoma, such as a chemotherapeutic agent. Finasteride is a non-limiting example of a suitable chemotherapeutic agent.

In other embodiments, the DDD comprises an immunotherapy agent (Guo et al and references therein; Clinical Immunotherapy Trials Network www.CITNinfo.com). Non-limiting examples of immunotherapy agents are ipilimumab (Yervoy; Bristol-Myers Squibb), sipuleucel-T (Dendreon Corp, Seattle, Wash.), IL-7, CP-870,893 (Pfizer), Allovectin-7 (Vical), BiovaxID (Biovest International), IMA901 (Immatics Biotechnologies GmbH), MAGE-A3 (GlaxoSmithKline), Multikine (CEL-SCI Corporation), NeuVax (Galena Biopharma), PROSTVAC (Bavarian Nordic A/S), Rindopepimut (CDX-110) (Celldex Therapeutics), Stimuvax (Oncothyreon and Merck KGaA), Talimogene laherparepvec (Amgen), and TG4010 (Transgene and Novartis). In certain embodiments, the immunotherapy agent does not comprise live cells.

Numerous types of immunotherapeutic agents have been developed, and a number of intratumoral immunotherapies are currently being examined in clinical trials (Cancer Immunotherapy Trial Network www.CITNinfo.org). Agents include T-cell and NK-cell growth factors like IL-15, others that stimulate T cells or activate dendritic cells, so-called immune checkpoint inhibitors like ipilimumab, and others that inhibit or neutralize factors secreted by tumors that suppress the immune system. Recently, two agents have been selected to be tested in CITN-led trials, selected from the 20 identified in the CITN 2007 workshop, IL-15 and a dendritic cell-activating monoclonal antibody called CP-870,893.

Immunotherapy agent interleukin-15 (IL-15) is a recombinant agent that is chemically identical or similar to the endogenous cytokine interleukin-15 (IL-15) with immunomodulating activity. IL-15, secreted by mononuclear phagocytes (and some other cell types) following viral infection, regulates T and natural killer cell activation and proliferation. This cytokine induces activation of transcription activators STAT3, STAT5, and STAT6 via JAK kinase signal transduction pathways in mast cells, T cells, and dendritic epidermal T cells.

CP-870,893 is a fully human monoclonal antibody (mAb) agonist of the cell surface receptor CD40 with potential immunostimulatory and antineoplastic activities. Similar to the CD40 ligand (CD40L or CD154), CD40 agonist monoclonal antibody CP-870,893 binds to CD40 on a variety of immune cell types, triggering the cellular proliferation and activation of antigen-presenting cells (APCs), activating B cells and T cells, and enhancing the immune response; in addition, this agent may activate CD40 present on the surfaces of some solid tumor cells, resulting in apoptosis and decreased tumor growth.

Dosage and Drug Percentage

A DDD of the described methods and compositions may, in certain embodiments, contain at least 10 µg siRNA. In other embodiments, the amount is between 10-2000 µg (inclusive) siRNA per device. In more specific embodiments, the amount is between 300-1700 (inclusive) µg siRNA per device. In still other embodiments, the amount is between 300-1100 (inclusive) µg siRNA per device. Alternatively, the amount is between 400-900 (inclusive) µg siRNA per device.

In yet other embodiments, the amount of said RNAi agent in all the DDD's administered as a batch (a single dose) is at least 4 µg, for example at least 5 µg, at least 6 µg, at least 7 µg, at least 8 µg, at least 10 µg, at least 12 µg, or at least 15 µg. In still other embodiments, the amount of RNAi agent present per dose is between 2-10 µg, inclusive, for example 2, 3, 4, 5, 6, 7, 8, 9, or 10 µg.

In yet other embodiments, all the DDD's administered as a batch deliver a dose of 0.008-0.065 mg/kg/month, inclusive, for example 0.008 mg/kg/month, 0.01 mg/kg/month, 0.015 mg/kg/month, 0.02 mg/kg/month, 0.03 mg/kg/month, 0.05 mg/kg/month, or 0.065 mg/kg/month.

In certain embodiments, the drug percentage of a device of the described methods and compositions is at least 20%. In another embodiment, the drug percentage is at least 30%, for example 30%, 35%, 40%, 45%, 50%, 55%, or 60%. In another embodiment, the drug percentage is between 8-30%, inclusive, for example 8%, 9%, 10%, 11%, 12%, 13%, 14%, 15%, 16%, 17%, 18%, 19%, 20%, 22%, 24%, 26%, 28%, or 30%. Some exemplary formulations are as follows:
64-76% PLGA; 16-27% drug; 5-12% mannitol; an exemplary specific formulation is 70% PLGA; 20% drug; 10% mannitol.

In still other embodiments, a DDD of the methods and compositions described herein comprises trehalose and does not comprise mannitol. In still other embodiments, the DDD comprises both trehalose and mannitol. In more specific embodiments, the DDD may contain 70-91.2% PLGA; 8-30% siRNA; 0.6-1.5% trehalose; and 0.1-0.4% sodium bicarbonate. In other embodiments, the DDD may contain 75-91.2% PLGA; 8-25% siRNA; 0.6-1.5% trehalose; and 0.1-0.4% sodium bicarbonate. In still other embodiments, the DDD may contain 80-91.2% PLGA; 8-20% siRNA; 0.6-1.5% trehalose; and 0.1-0.4% sodium bicarbonate. In yet other embodiments, the DDD may contain 85-91.2% PLGA; 8-15% siRNA; 0.6-1.5% trehalose; and 0.1-0.4% sodium bicarbonate. In additional embodiments, the DDD may contain 88-91.2% PLGA; 8-12% siRNA; 0.6-1.5% trehalose; and 0.1-0.4% sodium bicarbonate. In yet other embodiments, the DDD may contain 89-91% PLGA; 8-10% siRNA; 0.6-1.5% trehalose; and 0.1-0.4% sodium bicarbonate. In still other embodiments, the DDD may contain about 90% PLGA 85:15, about 9% siG12D, about 1% Trehalose, and about 0.2% NaHCO$_3$.

In other embodiments, the DDD has less than 5% trehalose, for example in different embodiments 0.5%, 1%, 1.5%, 2%, 2.5%, 3%, 3.5%, 4%, or 4.5%. Those skilled in the art will appreciate that the release profiles and efficacies of DDD's having varying percentages of trehalose can readily be tested in light of the information provided herein.

Sodium bicarbonate is an excipient that in some embodiments facilitates cavity formation. In other embodiments, sodium bicarbonate facilitates modulation of or decrease in pH. An exemplary specific formulation is 70% PLGA; 28% drug; 1% trehalose; 1% sodium bicarbonate and/or >1% of an excipient that facilitates modulation of decrease in pH.

In other embodiments, a trehalose-containing DDD is provided, comprising an siRNA against a target that is not a prostate-cancer-related target gene. In other embodiments, the DDD has less than 5% trehalose, for example in different embodiments 0.5%, 1%, 1.5%, 2%, 2.5%, 3%, 3.5%, 4%, or 4.5%.

Additional Features

In other embodiments, a DDD of the described methods and compositions is coated. A coating can be designed for a number of characteristics, including modulating the release rate or preventing protein stickiness during long-term storage. The coating in some embodiments comprises the same material used to form the matrix, for example a PLGA matrix, only without the drug. In other embodiments, the coating comprises a material similar to that used to form the matrix (for example containing the same building blocks in a different ratio, or containing the same polymer but with a different MW), only without the drug. In other embodiments, the coating comprises the same material used to form the matrix, together with at least one other polymeric material such as PEG. In other embodiments, the coating is selected from polylactic acid (PLA) and PLA:PGA (polyglycolic acid) in a ratio of at least 80:20, inclusive for example 80:20, 82:18, 84:16, 85:15, 86:14, 88:12, 90:10, 92:8, 94:6, 96:4, 98:2, and 99:1, and a MW greater than 50 KDa, for example 60 KDa, 70 KDa, 80 KDa, 100 KDa, 120 KDa, 1500 KDa, or 200 KDa). In more particular embodiments, the coating comprises PLGA in a ratio of at least 80:20, inclusive, having a MW of 50,000-100,000, inclusive.

In certain embodiments, DDD's of dimensions larger than ~0.8 mm can be identified by standard ultrasound (US). In other embodiments, materials to visualization in a medical or surgical procedure, for example CT, MRI or US visualization are included. Non-limiting examples of contrast agents are barium, diatrizoate, ethiodized oil, gallium citrate, iocarmic acid, iocetamic acid, iodamide, iodipamide, iodoxamic acid, iogulamide, iohexyl, iopamidol, iopanoic acid, ioprocemic acid, iosefamic acid, ioseric acid, iosulamide meglumine, iosemetic acid, iotasul, iotetric acid, iothalmic acid, iotroxic acid, ioxaglic acid, ioxotrizoic acid, ipodate, meglumine, metrizamide, metrizoate, propyliodone, and thallous chloride.

Figure 6:
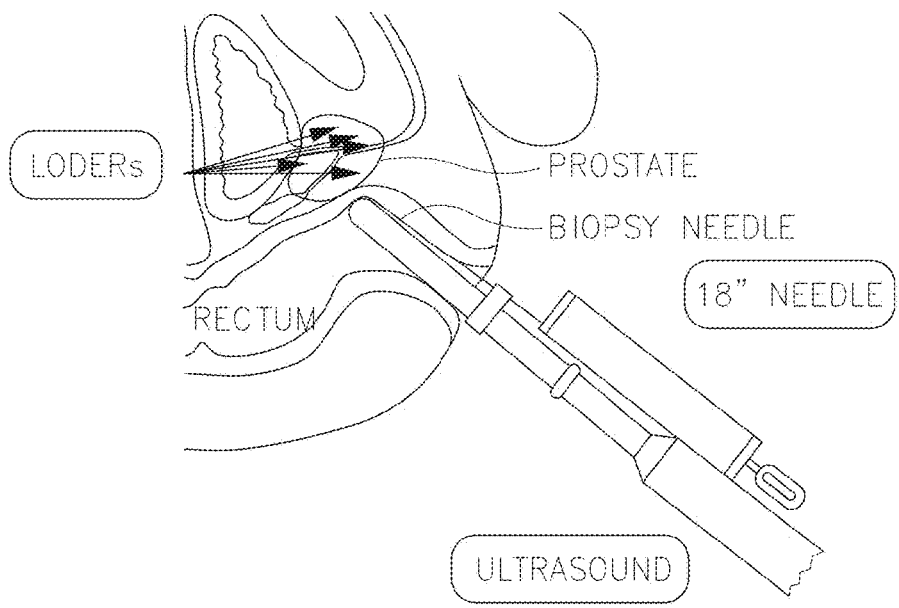
FIG. 6: shows implantation of DDDs in the external prostate using ultrasound biopsy procedure.
Figure 7:
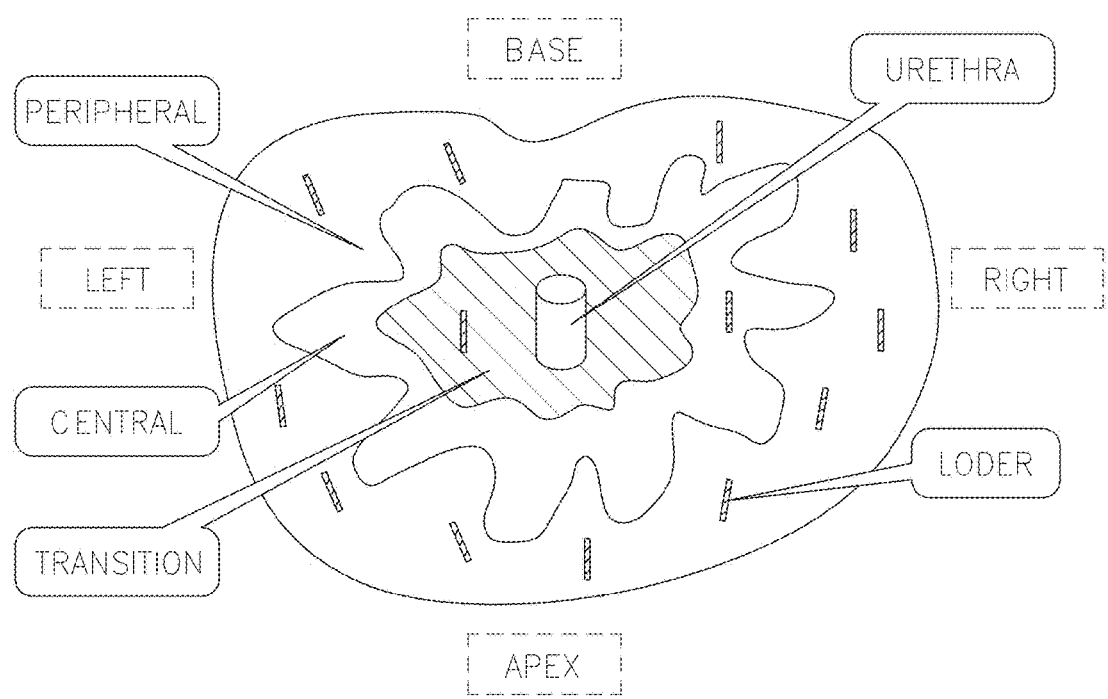
FIG. 7: shows an example of distribution of DDDs in an exemplary protocol, mainly in the peripheral zone.
Figure 8:
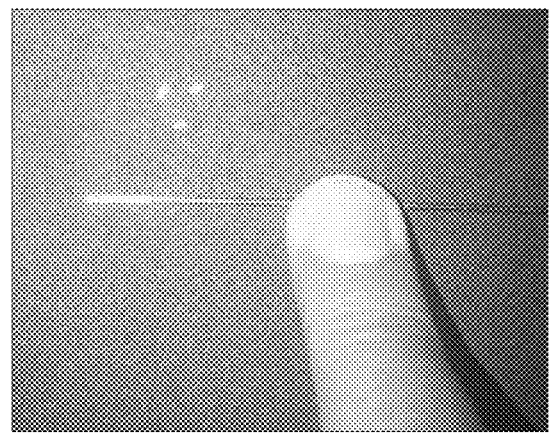
FIG. 8: shows a picture of the distal end of an 18-gauge biopsy needle and DDDs of dimensions 0.8 mm×1.7 mm.

Activating Device:

Some embodiments include activation via an external device, such as a radiation source or an ultrasound probe, to affect drug release, and/or penetration into cells. Activation can be performed along the time span of the DDD, at a single or several defined time points. The protocol defining such time points can be based on a pre-defined treatment plan and/or changes in patient read-outs. FIG. 6 depicts implantation of DDDs in the external prostate using the ultrasound biopsy procedure. FIG. 7 depicts an exemplary distribution of DDDs, mainly in the peripheral zone.

Other embodiments provide methods of making DDDs described herein. Methods of making various DDD's similar to those presented herein are described in US Patent Application Pub. No. 2011/0195123.

Therapeutic Methods

Also provided herein is a device described herein for treating a prostate carcinoma. In certain embodiments the subject is a human patient. In other embodiments, the subject is a veterinary patient.

In some embodiments, patients treated by the described methods have prostate carcinoma. In more specific embodiments, the patients have a Gleason score between 5-7, inclusive, more preferably 6. In other embodiments, the patients have a PSA level of below about 10 ng/ml (nanograms per milliliter). In other embodiments, they have both a Gleason score of between 5-7, inclusive, more preferably 6, and a PSA level of below 10 ng/ml.

In certain, more specific embodiments, the DDD is designed for implantation into a subject using a biopsy needle via an ultrasound probe. Prostate biopsy is a well-known procedure to those skilled in the art. In certain, still more specific embodiments, the needle is a straight 18 gauge needle, and the number of DDDs implanted is between 8-12, inclusive, for example 8, 9, 10, 11, or 12.

In other embodiments, the DDD is designed for implantation into a subject using a prostate brachytherapy needle. Prostate brachytherapy is a well-known procedure to those skilled in the art. It is described, for example, in paragraph 0142 of US Patent Application Pub. No. 2011/0195123.

In other embodiments, the DDD is designed for implantation into a subject using a delivery device as described in International Patent Publication No. WO 2010/086849 to Silenseed LTD, the contents of which are incorporated herein by reference.

In another embodiments the drug load in DDD is between 150-300 µg, in another embodiment about 200 µg, per mm length of the DDD.

In other embodiments, a method is provided of treating a subject having prostate carcinoma, comprising the steps of implanting in the subject a DDD described herein.

In certain, more specific embodiments, the DDD is implanted into the subject using a biopsy needle.

In still more specific embodiments, 8-32 DDD per patient are implanted, for example 8, 9, 10, 12, 14, 16, 18, 20, 22, 24, 26, 28, 30, or 32 DDD. In yet more specific embodiments, 12 DDD per patient are implanted.

In other embodiments, the DDD is implanted into the subject using a prostate brachytherapy needle. In some embodiments, patients are implanted with 12 DDD's per treatment using a straight 18 gauge prostate biopsy needle under ultrasound visualization, using the existing transrectal ultrasound and biopsy protocol. The treatment achieves about $3 \times 10^8$ siRNA molecules per cell for a tumor containing $10^9$ cells.

The following steps are performed as one possible exemplary protocol that may be used: This procedure makes use of a needle apparatus containing a hollow beveled straight needle and an inner straight stylet, for example with a rounded head, both of dimension about 30 cm and of 18 gauge diameter. Unlike existing biopsy needles, for example Pro-Mag™ 18 G×30 cm of Angiotech Inc, the needle preferably has no 'biopsy gun' but a basic handle, and a port at its proximal end enabling loading of implants. An additional embodiment is a single needle device combining the two functions of biopsy sampling and DDD implantation. In such a single device the biopsy sampling is based on aspiration. In another embodiment the biopsy sampling is by harvesting histological specimens as is done, for example, with the Tru-Cut® sampling apparatus:

Identify the location of the prostate by transrectal US.
Insert biopsy needle apparatus into endoscope and connect.
Progress the needle apparatus through the scope into the prostate.
Fix the needle.
Withdraw the stylet.
Load the needle with DDDs at the stylet hub.
Insert the stylet or optionally a dedicated blunt stylet, and slide DDDs to the distal end.
Place DDDs at the cylindrical cavity created by the needle
Repeat the procedure for implanting more DDDs.
Retract the needle
Withdraw the system out of the US.
Withdraw US The DDD's are in some embodiments distributed isotropically, but with special care not to puncture the central zone and urethra, and in general not in the inner zones, rather solely or primarily in the peripheral zone.

In other embodiments, the DDD is implanted into the subject using a delivery device as described in WO 2010/086849 to Silenseed Ltd.

In other embodiments, a method of treating cancer is provided, comprising the step of administering to a subject one or more DDD's described herein, comprising one or more delayed-release DDD. In other embodiments, a combination of DDD's is administered, comprising both (a) one or more delayed-release DDD and (b) one or more DDD that is not delayed release. In some embodiments, the cancer is a prostate carcinoma. In other embodiments, the cancer is another cancer. In some embodiments, the cancer is selected from a pancreatic tumor, a colon tumor, a lung tumor, brain cancer, liver cancer, kidney cancer, melanoma, endometrial carcinoma, gastric carcinoma, renal carcinoma, biliary carcinoma, cervical carcinoma, and bladder carcinoma. In more specific embodiments, the cancer is selected from pancreatic carcinoma, pancreatic ductal adenocarcinoma, small-cell lung carcinoma, and colorectal cancer. Provision of a combination of delayed-release and non-delayed-release DDD's in some embodiments enables a longer time course of significant siRNA release, without the need for repeated therapeutic intervention.

In other embodiments, a trehalose-containing DDD, as described herein is administered, to treat a cancer other than prostate cancer. In some embodiments, the cancer is selected from a pancreatic tumor, a colon tumor, a lung tumor, brain cancer, liver cancer, kidney cancer, melanoma, endometrial carcinoma, gastric carcinoma, renal carcinoma, biliary carcinoma, cervical carcinoma, and bladder carcinoma. In more specific embodiments, the cancer is selected from pancreatic carcinoma, pancreatic ductal adenocarcinoma, small-cell lung carcinoma, and colorectal cancer.

Animal and Human Testing

In animal models, tumor progress may be monitored by any method known in the art. One method is by removing and weighing the tumor. This may be done, for example, by weighing slices after histology slice preparation.

The presence and amount of therapeutic siRNA in tissue samples may be determined by any method known in the art, for example by a method described herein. RNA quantity may be assessed, for example, by Nanodrop, and RNA quality by gel electrophoresis. RNA quantity may also be assessed by PCR, e.g. real-time PCR, Northern blot, HPLC, MSLC (Membrane surface liquid culture), or in situ hybridization.

Excised tumor tissue from human or animal studies may be preserved by any method known in the art, for example by freezing in liquid nitrogen (for subsequent studies requiring live cells), or may be fixed, for example in paraformaldehyde solution.

Characterization of tissue samples may include various methods known in the art, including but not limited to hematoxylin and eosin staining, immunohistochemistry staining, and measuring levels of gene products, such as the genes targeted by the therapeutic siRNA, in some cases in the presence of an internal control.

In other cases, the effects of devices described herein on the excised tissue sample may be studied, for example in an experimental animal or in culture.

EXAMPLES

Example 1: Production of DDD's Containing Anti-Prostate Cancer RNAi Molecules DDD's containing anti-prostate cancer RNAi molecules were produced in a biological-class hood in a clean room, as follows:

Step 1: Preparation of siRNA/D-Mannitol/Sodium Bicarbonate mixture: siRNA was added to the pre-weighed D-Mannitol and Sodium Bicarbonate, and they were dissolved in RNase-free sterile water.

Step 2: Freezing: The liquid was placed into glass vials, frozen in dry ice, and lyophilized for 48 hours.

Step 3: PLGA Preparation: PLGA was dissolved in Ethyl Acetate.

Step 4: Combining PLGA with D-Mannitol/Sodium Bicarbonate/siRNA: The PLGA solution was poured into the glass vial containing the lyophilized D-Mannitol/Sodium Bicarbonate/siRNA in fractions and stirred until homogenization Step 5: Solvent evaporation. The solution was poured into a Teflon-covered dedicated glass dish and left to evaporate inside a dedicated container for 3-5 days.

Step 6: Release of film: The film was released from the glass dish using tweezers and a scalpel.

Step 7: Excision of individual DDDs: Individual DDDs were excised using a dedicated puncher. Each DDD was of a cylindrical shape, with a length and diameter of ~1.3 mm and ~0.6 mm, respectively.

Example 2: In Vitro Testing of Release Characteristics of DDDs

Figure 2A:
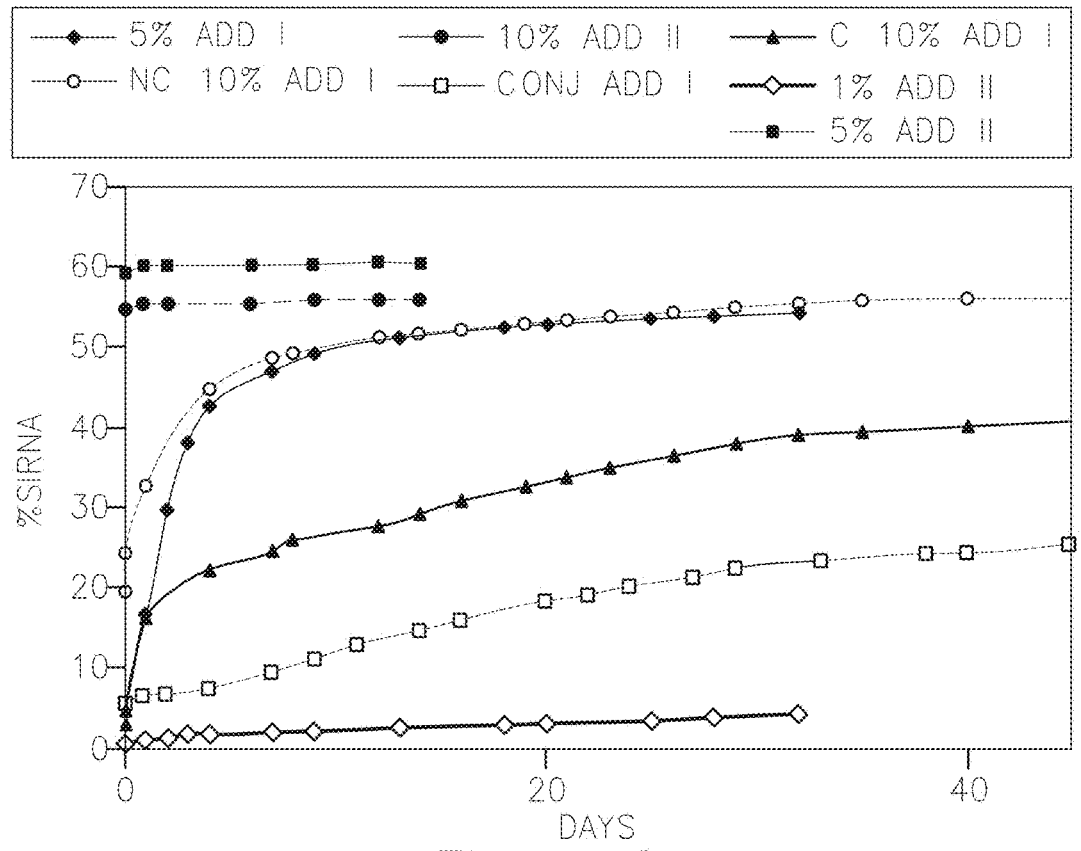
FIGS. 2A-2B show working examples of siRNA release in PBS and its dependence on coating, additives, percent of additives, and conjugation.
Figure 2B:
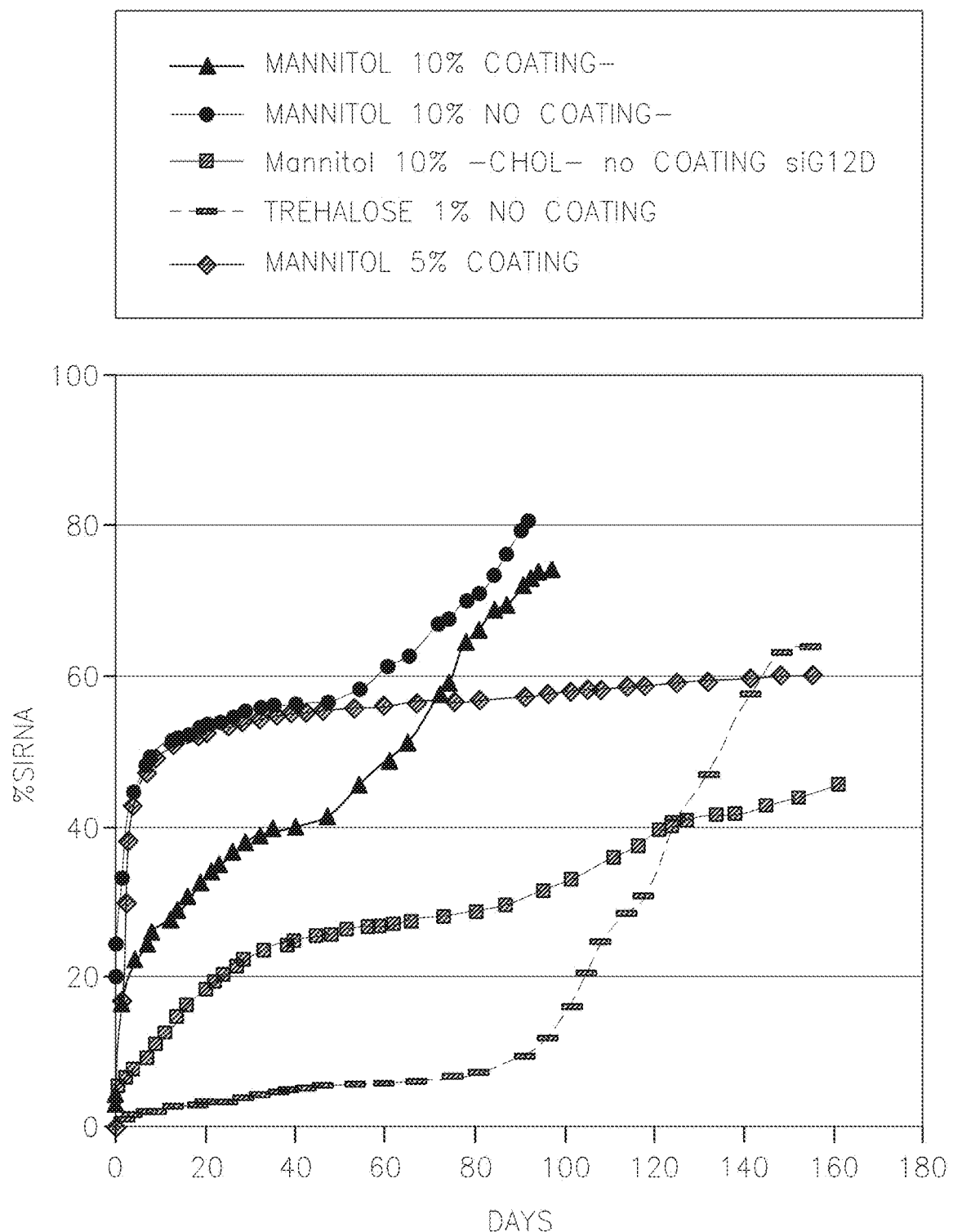

FIG. 2 describes variations in release characteristics that were achieved by varying the composition of DDDs. The curve "1% add II" provides a working demonstration of very slow release that can last 6 months, for example using PLGA of high PLA:PGA ratio, such as 90:10, and MW (molecular weight) higher than 50 KDa.

The following protocol was used to make the DDD, covering all cases in FIG. 2:

1. Mix siRNA 40 mg (naked, 5'-chol) RNAse free water solution with 1% NaHCO$_3$ (Sigma) and with Mannitol (10% or 5%) or Trehalose (10%, 5% or 1%) and lyophilize overnight.
2. Weight 450 mg PLGA 85:15 (Boehringer-. Ingelheim), add to the lyophilized powder and mix. The viscosity of the PLGA was 0.63-0.67 dl/gr, and its estimated MW was 60,000-80,000.
3. Add Ethyl acetate (~1.5 ml) (Sigma) and mix to get clear white solution.
4. Pour onto Teflon covered glass dish (D=2 cm).
5. Dry (5-7 days) to get a film.
6. Punch the film with 19G puncher to get 19 G DDDs.

PLGA Coating:
1. Dissolve PLGA 85:15 30% in Ethyl acetate and drip onto each DDD.
2. Push the DDDs out of the drop after 2 sec.
3. Dry.

Measurements of release were done by Nanodrop at a specific wavelength of 260 nm and/or 230 nm. Measurements were taken at time points of 0 h, 4 h, 12 h, 24 h, 3 d, 7 d, 2 w, 4 w, 6 w, and 8 w, and, in some experiments, at additional time points after and between these times. Each measurement utilized 1.5 microliters (μL) of siRNA solution (PBS or water) and results are given in nanogram/microliter. Prior to each measurement, a null measurement of solution only (PBS) was performed for subtraction. Each time point contained five parallel measurements (from five different DDDs). Presented in FIGS. 1-2 are the averages of such five points.

Example 3: Testing of Targets in Cell Culture

Methods
Viability Test

PC3 cells were seeded on 96-well plates one day before transfection. Transfection was performed using Lipofectamine 2000 transfection reagent, according to the manufacturer's protocol. siRNAs were used at the indicated concentration. Scrambled non-targeting siRNA was used as transfection control. 72 hrs post transfection, viable cells were fixed and stained by Methylene Blue (MB). Relative cell amounts were assessed using a microplate absorbance reader. The results are presented relative to cells transfected with scrambled siRNA.

Methylene Blue (MB) Assay

The protocol was adapted from Oliver et al.

Cells were seeded in a 96-well plate, then treated as follows:
1. Remove medium from plate.
2. Wash cells twice with PBS (250-400 ul)
3. Fix cells: Add 100-μl 4% formaldehyde. Keep at room temperature for 20 min or for up to several weeks at +4° C. (cold room, wrapped so the liquid will not evaporate).
4. Wash twice with PBS (250-400 μl).
3. Wash cells twice with 200 μl 0.2M borate buffer, pH 8.5.
4. Stain cells with 50 μl 1% Methylene blue in borate buffer. Incubate for 20 min at room temperature.
5. Wash with tap water until control well (without cells) is white.
6. Color elution: add 100 μl 0.1M HCl. Incubate at room temperature for at least 2 hrs, up to overnight (wrapped so the liquid will not evaporate)
7. Measure OD at 585 nM.

0.2M borate buffer pH 8.5: Add 7.628 gr/100 ml of borate (sodium tetraborate) (Na$_2$B$_4$O$_7$.10H$_2$O; MW 381.3) and 1.2378 gr/100 ml boric acid (H$_3$BO$_3$; MW 61.83). Titrate with NaOH if needed.

0.1M HCl: 50 ml DDW+0.5 ml 37% HCl (=10.1 M)

PBS solution: 0.26 g KH$_2$PO$_4$, 2.17 g Na$_2$HPO$_4$·7H$_2$0, and 8.71 g NaCl in 800 mL dH$_2$0. Adjust pH to 7.4 and bring volume to 1 L with dH$_2$0.

Results

PC3 cells (ATCC #CRL-1435) were grown and tested for mycoplasma contamination, and were found to be mycoplasma free.

Figure 3:
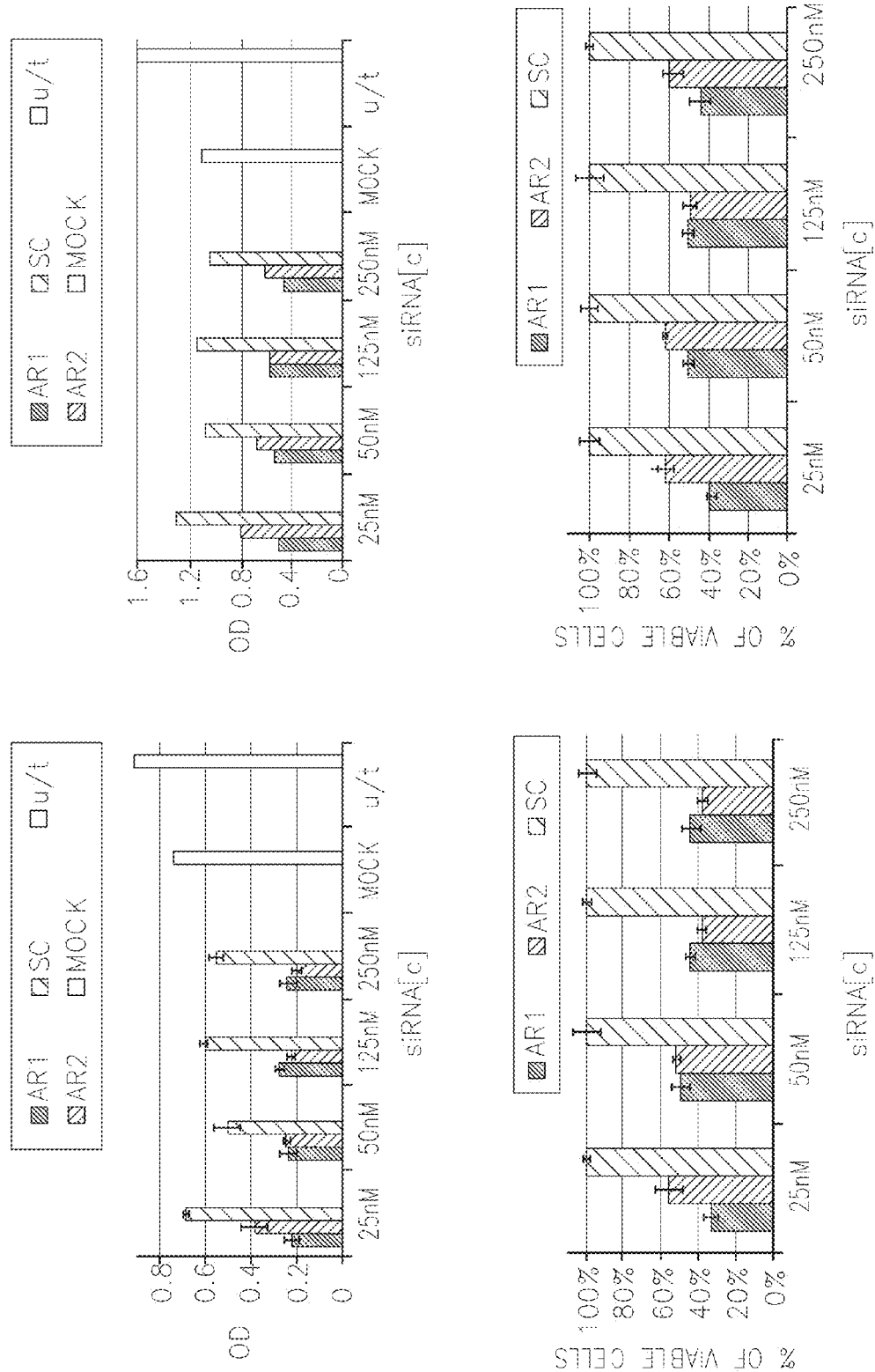
FIG. 3: shows the effect of down-regulation of Androgen Receptor (AR), by two different siRNA sequences, on cell viability of PC3 prostate cancer cells. Also shown are the calibration and selection of siRNA doses. AR1 & AR2 refer to siAR-1 and siAR-2, respectively. Mock=mock-transfected; u/t=untransfected; SC=scrambled (non-specific) siRNA. Testing was done at $0.5 \times 10^4$ (left panels) and $0.75 \times 10^4$ (right panels) cells/well. Vertical axis: upper panel—OD; lower panel—percentage of viable cells (calculated relative to mock transfected cells). Horizontal axis: siRNA concentration. All changes were significant, with a p value of less than 0.001.

Viability testing was done by the MB assay. Based on growth calibration, two cell concentrations of 0.5 and 0.75× $10^4$ cells/well were tested with two AR siRNAs. For transfection calibration, cells were seeded at the indicated concentration and transfected at the indicated siRNA concentrations. The optimum concentration was found to be 125 nM, which corresponds to 0.375 µg siRNA/well (FIG. 3).

Figure 4A:
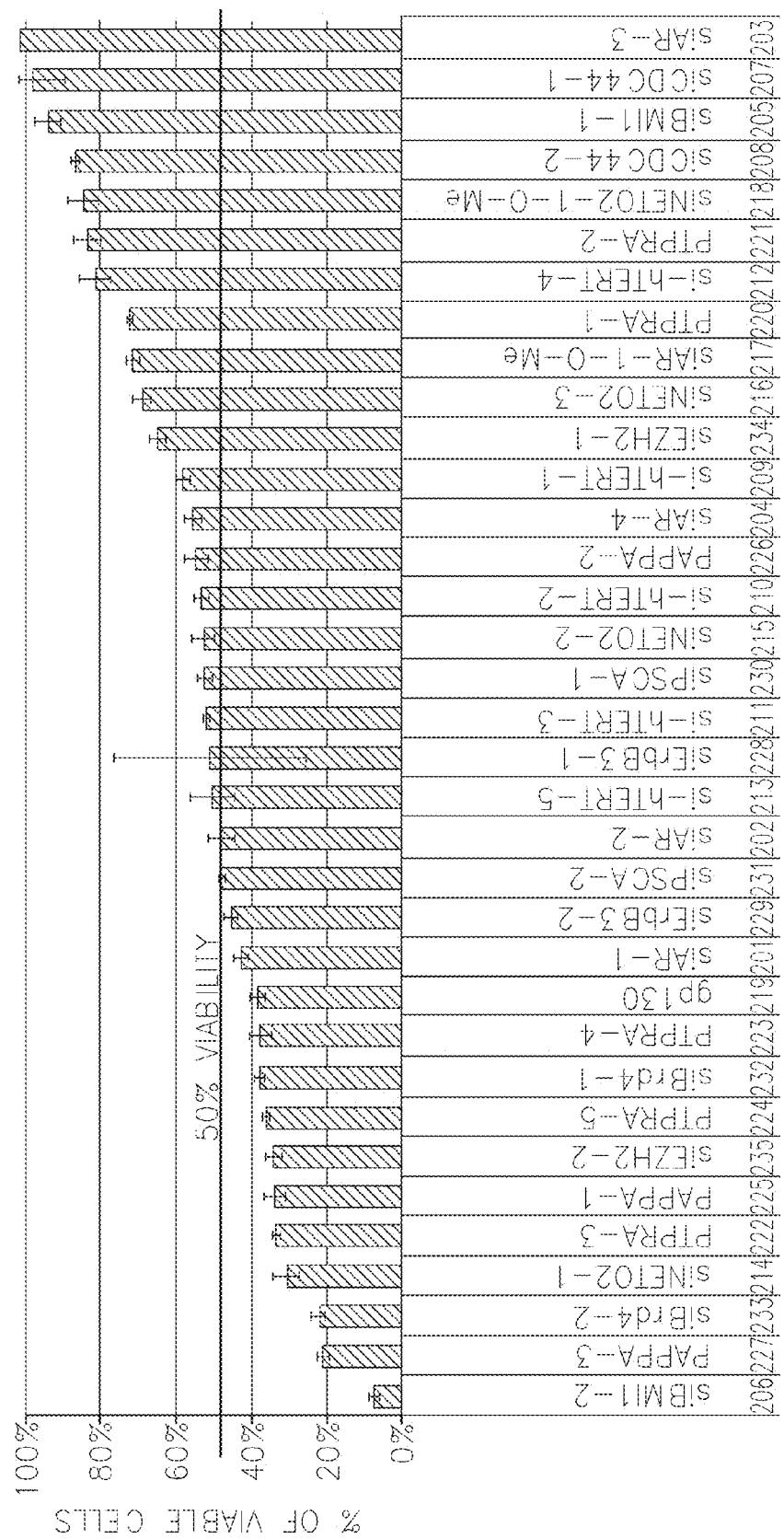
FIGS. 4A-4D show the effect of treatment by various siRNA on viability of PC3 cells, ordered by efficacy (FIG. 4A), and on mRNA levels (FIGS. 4B-4D). PC3 were seeded in 6-well plates one day before transfection. Transfection was performed using Lipofectamine 2000 transfection reagent. The indicated siRNas were used at a 150 nM concentration, which is 6-µg/well. Scrambled (non-targeting) siRNA was used as a transfection control. For the viability test, cells were grown for 72 hrs, fixed in 4% PFA and stained as by Methylene blue (MB). Percentage viability was normalized to the viability of the scrambled-transfected cells. In each case, the difference between the siRNA-treated cells and the scrambled-transfected cells was significant when compared to the difference between the quadruplicate samples. For RNA quantization, 24-hrs post-transfection, total RNA was purified using Trizol® reagent (Invitrogen™). cDNA was prepared using qScript™ cDNA Synthesis kit (Quanta Biosciences). Relative mRNA level was assessed compared to HPRT endogenous control using the Image Gauge computer program.

Next, viability testing was performed with siRNA molecules targeting various prostate carcinoma-related genes. As shown in Table 4 and FIG. 4A, many of the constructs caused growth inhibition. Notably, the 2-O-Me-modified constructs retained a significant amount of activity. Their relative activity compared to non-modified constructs is expected to be greater in vivo, where their resistance to nucleases will be manifested.

Figure 4B:
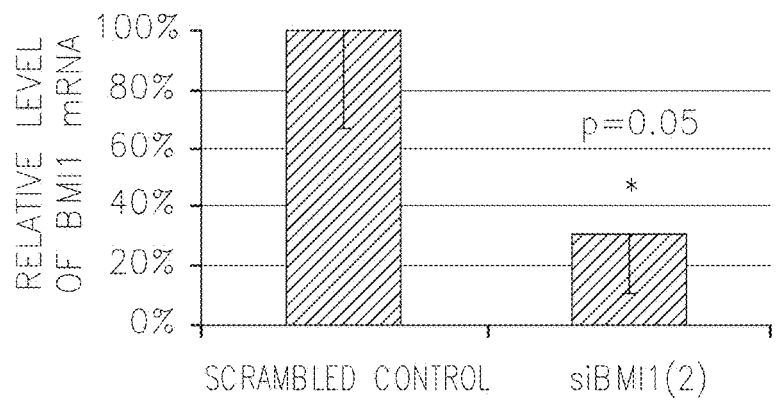
Figure 4C:
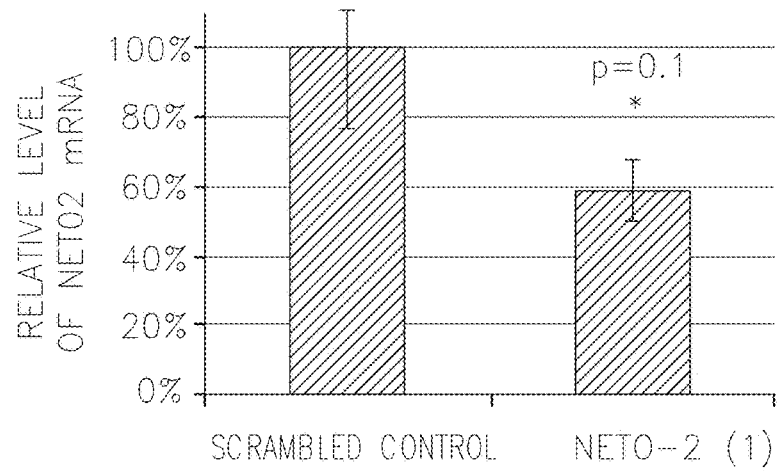
Figure 4D:
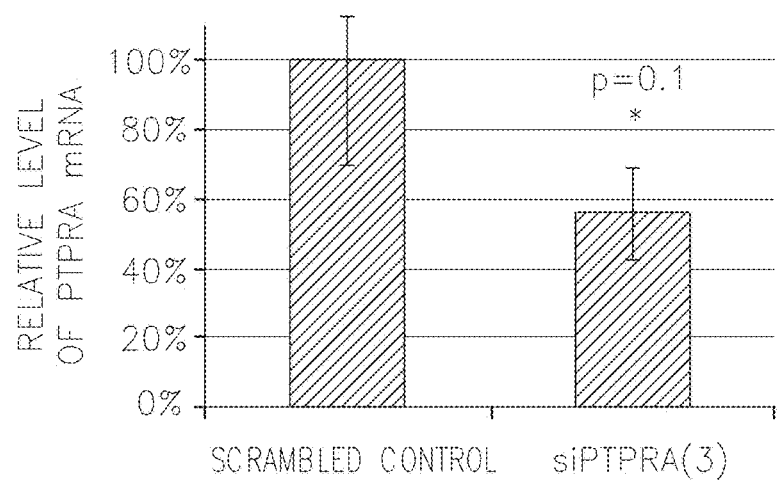

Furthermore, the effects of anti-BMI-1-2, anti-NETO2-1, and anti-PTPRA-3 on the levels of their target genes were assessed. Each tested siRNA caused a significant decrease in the level of the target (FIGS. 4B-D).

TABLE 4

Viability testing of PC3 cells treated with prostate carcinoma-specific siRNA's.

| target | siRNA-no. | siRNA-name | Average percentage of viable cells | stderr % |
|---|---|---|---|---|
| Androgen receptor | 201 | siAR-1 | 43% | 2% |
| | 202 | siAR-2 | 48% | 4% |
| | 204 | siAR-4 | 55% | 2% |
| | 203 | siAR-3 | 111% | 1% |
| | 217 | siAR-1-O-Me | 71% | 2% |
| BMI1 | 205 | siBMI1-1 | 94% | 4% |
| | 206 | siBMI1-2 | 7% | 1% |
| Brd4 | 233 | siBrd4-2 | 22.2% | 1.7% |
| | 232 | siBrd4-1 | 37.6% | 1.5% |
| CDC44 | 207 | siCDC44-1 | 98% | 8% |
| | 208 | siCDC44-2 | 87% | 1% |
| EtbB3 | 229 | siErbB3-2 | 45.2% | 1.8% |
| | 228 | siErbB3-1 | 50.9% | 25.5% |
| EZH2 | 235 | siEZH2-2 | 34.0% | 2.0% |
| | 234 | siEZH2-1 | 64.8% | 2.1% |
| gp130 | 219 | gp130 | 38% | 2% |
| hTERT | 213 | si-hTERT-5 | 50% | 6% |
| | 211 | si-hTERT-3 | 52% | 1% |
| | 210 | si-hTERT-2 | 53% | 2% |
| | 209 | si-hTERT-1 | 58% | 2% |
| | 212 | si-hTERT-4 | 81% | 4% |
| NETO2 | 214 | siNETO2-1 | 31% | 3% |
| | 215 | siNETO2-2 | 53% | 3% |
| | 216 | siNETO2-3 | 69% | 3% |
| | 218 | siNETO2-1-O-Me | 84% | 4% |
| PAPPA | 227 | PAPPA-3 | 21% | 2% |
| | 225 | PAPPA-1 | 34% | 3% |
| | 226 | PAPPA-2 | 54% | 3% |
| PSCA | 231 | siPSCA-2 | 47.6% | 1.0% |
| | 230 | siPSCA-1 | 52.3% | 1.8% |
| PTPRA | 222 | PTPRA-3 | 33% | 1% |
| | 224 | PTPRA-5 | 36% | 1% |
| | 223 | PTPRA-4 | 38% | 3% |
| | 220 | PTPRA-1 | 72% | 1% |
| | 221 | PTPRA-2 | 84% | 4% |

Example 4: Manufacturing and Testing of Trehalose-Containing DDD's

1% Trehalose-containing DDD's were produced as follows:
1. Dissolve 40 mg siG12D (BioSpring GmbH) in 2 ml DNAse/RNAse free water.
   The sequences of the sense and antisense strands of siG12D were GUUGGAGCUGAUGGCGUAGdTdT (SEQ ID No: 108), and CUACGCCAUCAGCUCCAACdTdT (SEQ ID No: 109), respectively.
2. Add siRNA solution to pre-weighed Trehalose (4 mg.) and $NaHCO_3$ (1 mg) and vortex for several min.
3. Freeze solution of siG12D, Trehalose and $NaHCO_3$ in liquid nitrogen and lyophilize for 48 h.
4. Combine 400 mg of lyophilized PLGA with the lyophilized siG12D, Trehalose and $NaHCO_3$ powder and mixed.
5. Dissolve the mixed powder in 1.5 ml Ethyl acetate to obtain a milky solution. Mix and pour into a Teflon-covered glass dish, diameter 2 cm.
6. Dry for 3 days to obtain a film.
7. Punch the film to obtain DDD's.

The final composition was 89.89% PLGA 85:15 (supplier: Boehringer Ingelheim Pharma GmbH), 9% siG12D, 1% Trehalose, and 0.22% $NaHCO_3$. DDD dimensions were 2-3 mm×1 mm.

The release profiles of DDD's were measured in vitro at 37° C. in PBS and in vivo. For in vivo testing, C57bl/6 mice were anesthetized using ketamine and xylazine (for a 25-gram mouse, a 50 µl intra-peritoneal injection of 0.9 ml ketamine+0.1 ml xylazine). The DDD's were inserted subcutaneously into a minimal incision made in the skin.

Release in vitro was quantified using a Nanodrop® apparatus. For validation, release from in vivo trials was also quantified by electrophoresis in a 10% urea-acrylamide gel. Gels were visualized using Pharmacia Biotech ImageMaster™ VDS (cat #80-6246-82) and quantified using Image-Gauge software.

Figure 5:
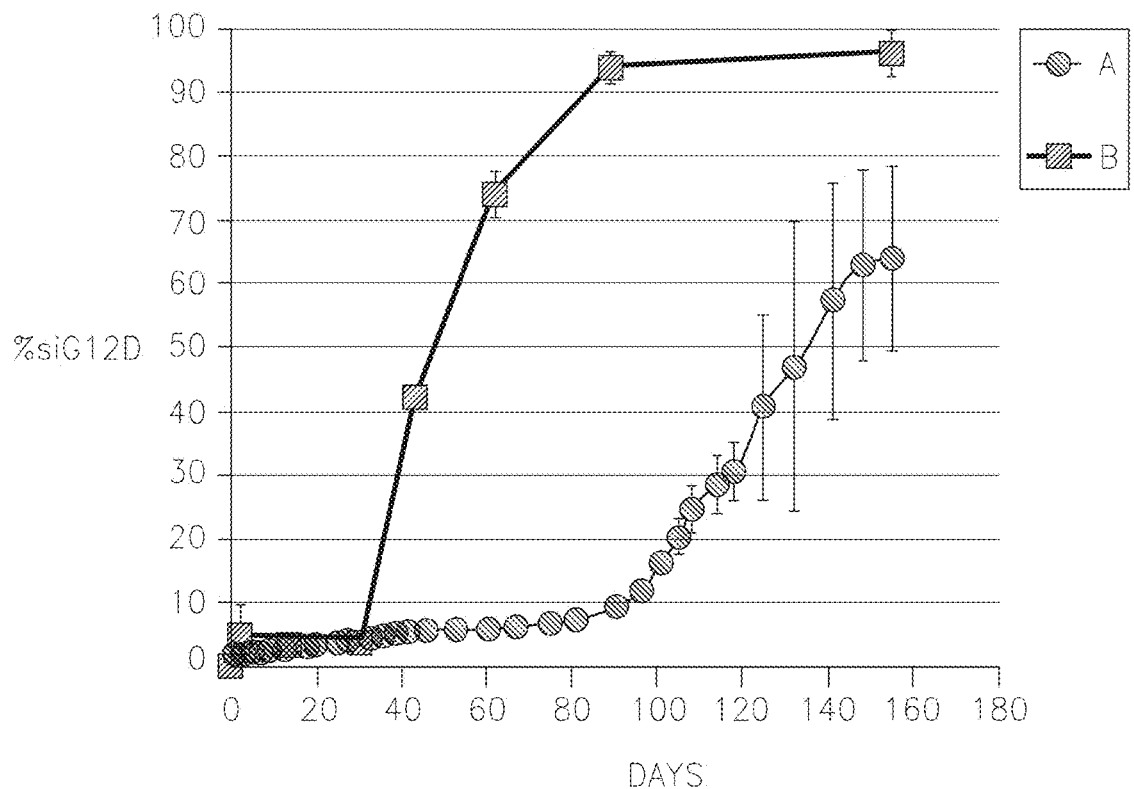
FIG. 5 shows release profiles of DDDs that 'hibernate' (do not release a significant amount of drug) during an initial period. In the depicted examples, the cumulative drug released during the first three months is less than ~10% (in vitro at 37° C. in PBS; data set A) and/or the release during the first month is less than ~5% (in vivo, inside a mouse; data set B). The DDDs contain trehalose.

In vitro, the trehalose-containing DDD's exhibited delayed release, with less than 10% of the siRNA released after 90 days, followed by a steady release of the next 55% of the siRNA over the next 70%. In vivo, these DDD's steadily released about 90% of the siRNA over the first 90 days, followed by a slower release of most of the remaining siRNA over the next 70 days (FIG. 5).

Example 5: Effect of Anti-BMI-1 and Anti-hTERT siRNA on Various Cancer Cell Lines Anti BMI-1 (si-BMI1) and anti-hTERT siRNAs were administered to several cancer cell lines, and the effect on cell viability was tested. The cell lines used included prostate, pancreas, colon (two lines), lung (two lines), neuroblastoma, embryonic kidney, and hepato-cellular carcinoma lines, as follows:
PC3 Human prostate adenocarcinoma.
Panc1 Human pancreatic ductal carcinoma.
HT29 Human colorectal adenocarcinoma.
H460 Human large cell lung carcinoma.
SHY86 Human neuroblastoma.
HEK293T Human embryonic kidney.
Huh7 Human hepatocellular carcinoma.
H1299 Human non-small cell lung carcinoma.
RKO Human colon carcinoma.

Figure 10:
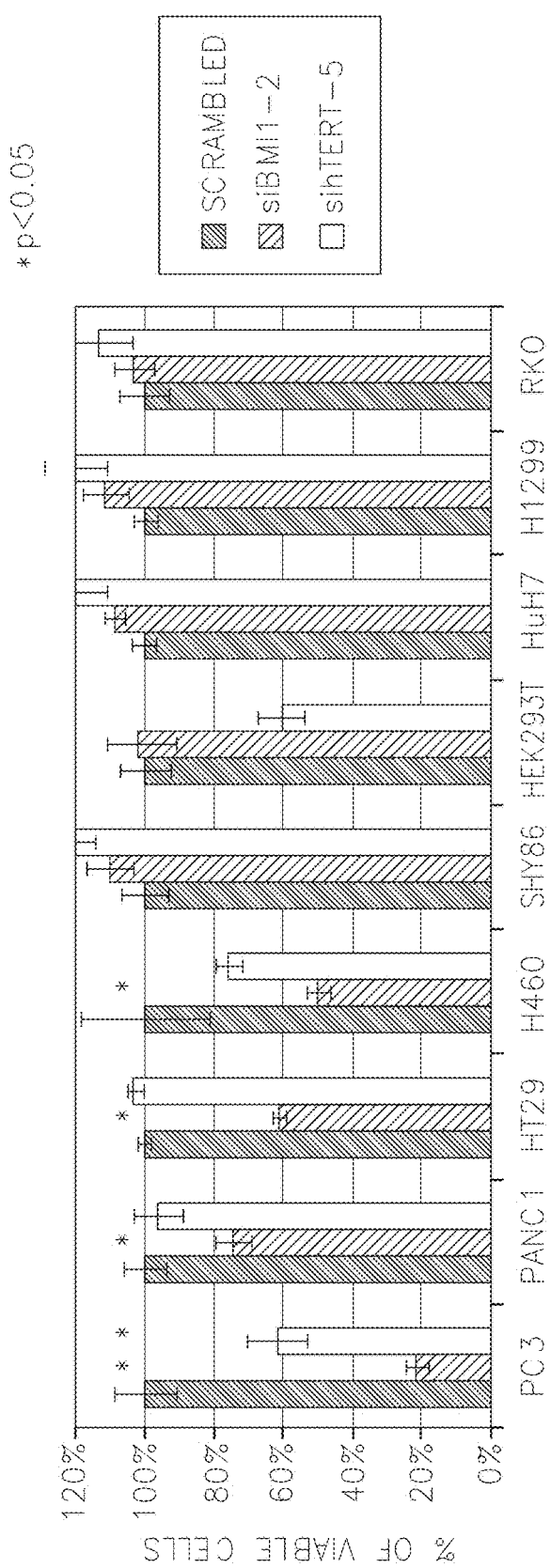
FIG. 10: Effect of anti BMI-1 (si-BMI1) and anti-hTERT siRNA on cell viability in several cancer cell lines, namely prostate, pancreas, colon (two lines), lung (two lines), neuroblastoma, embryonic kidney, and hepato-cellular carcinoma.

Experimental Description:

The indicated cell lines were seeded in a 96-well plate one day before transfection. Transfection was performed using Lipofectamine 2000 transfection reagent. The indicated siRNAs were used at a 125-nM concentration, which is 0.375-μg/well. Scrambled non-targeting siRNA was used as transfection control. 72 hrs post-transfection the reaction was stopped, viable cells were fixed and stained by Methylene Blue. Relative cell amounts were assessed using a microplate absorbance reader) (Tecan Group Ltd, model Infinite F50), and data was processed using the Magellan program (Tecan). The siRNA's were each effective in a number of cancer cell lines (FIG. 10). The results are presented relative to scrambled siRNA-transfected cells.

Example 6: Further In Vitro Testing of Targets

Following transfection with siRNA, siRNA functionality is measured by proliferation assay, colony-forming assay, and in other experiments by scratch assay, for example in PC3 cells, LNCaP cells, DU145 cells, or one or more of the other cell lines mentioned herein. In some experiments, kinetic studies are performed.

In other experiments, target mRNA inhibition is measured, for example using semi-quantitative PCR or quantitative PCR.

In other experiments, the effect on target protein level is measured, for example by Western blotting.

In other experiments, the stability of siRNAs in a RNase-rich environment is studied by incubation in a RNase-rich environment, followed by analysis of siRNA content, for example by gel electrophoresis.

In other experiments, siRNAs are modified to improve their stability and functionality, and their efficacy and stability are tested.

In other experiments, the release rate of siRNA is determined, for example using the methods described herein.

In other experiments, the effect of the siRNA's is tested in cancer stem cells, for example by colony forming ability, proliferation assay, or apoptosis assay.

Example 7: In Vivo Testing of DDDs Against Prostate Cancer

One or more DDDs are implanted in a mouse xenograft tumor model or other suitable model for prostate carcinoma. Tumor progress and/or the amount of therapeutic siRNA are monitored by methods known in the art. In some experiments, measurement of tumor volume is used to follow tumor growth. In other experiments, the survival of mice bearing the tumor is followed.

In other experiments, an orthotopic model is utilized to follow tumor growth during and after treatment with siRNA's.

Example 8: Testing of DDDs Against Prostate Cancer in Humans

Humans with prostate cancer are implanted with DDD's described herein, and the anti-tumor activity is tested. In some experiments, patients having a Gleason score of ~6 and PSA up to 10 are selected.

Example 9: Testing of Trehalose-Containing DDDs

Trehalose-containing DDDs are tested in an animal model, or in other experiments in human subjects, using an appropriate experimental setup, relative to mannitol-containing DDD's. Impaired tumor growth is indicative of enhanced therapeutic efficacy.

Example 10: Testing of Delayed-Release DDDs

Delayed-release DDDs are tested in an animal model, or in other experiments in human subjects, using an appropriate experimental setup, relative to non-delayed-release DDDs. In some experiments, delayed-release DDDs are implanted together with non-delayed-release DDDs, and are compared to non-delayed-release DDDs alone. siRNA release and tumor progression are monitored. A longer time course of significant siRNA release and/or impaired tumor growth are indicative of enhanced therapeutic efficacy.

It will be apparent that the precise details of the methods and compositions described herein may be varied or modified without departing from the spirit of the described invention. We claim all such modifications and variations that fall within the scope and spirit of the claims below, including all equivalents thereof.

REFERENCES

1. Biodegradable Intraprostatic Doxorubicin Implants, Ronnie Ortiz, 1,2 Jessie L-S. Au, 1,3 Ze Lu, 1,4 Yuebo Gan, 1 and M. Guillaume Wientjes. *The AAPS Journal* 2007; 9(2) Article 27.

2. Drug Resistance and the Solid Tumor Microenvironment Olivier Tredan, Carlos M. Galmarini, Krupa Patel, Ian F. Tannock, *J. Natl Cancer Inst* 2007; 99:1441-54.

3. Bergan and Scheidt, Inhibition And Treatment Of Prostate Cancer Metastasis. US Application Pub. No. 2009/0124569.

4. Patrawala et al, Highly purified CD44+ prostate cancer cells from xenograft human tumors are enriched in tumorigenic and metastatic progenitor cells. *Oncogene* (2006) 25:1696-1708).

5. M. H. Oliver et al, "A rapid convenient assay for counting cells cultures in microwell plates: application for assessment of growth factors." *Journal of Cell Science* 92, 513-519 (1989).

6. Guo et al., In situ vaccination with CD204 gene-silenced dendritic cell, not unmodified dendritic cell, enhances radiation therapy of prostate cancer." *Molecular Cancer Therapeutics*, Mol Cancer Ther. 2012 Nov. 6. [Epub ahead of print].

7. Terrone et al, Penetratin and related cell-penetrating cationic peptides can translocate across lipid bilayers in the presence of a transbilayer potential. Biochemistry. 2003 Dec. 2; 42(47):13787-99.

8. Magzoub et al, Interaction and structure induction of cell-penetrating peptides in the presence of phospholipid vesicles. *Biochim Biophys Acta*. 2001 May 2; 1512(1): 77-89.

9. Pooga et al, Cell penetration by transportan. FASEB J. 1998 January; 12(1):67-77.

We claim:

1. A millimeter-scale drug delivery device (DDD) comprising:
   A biodegradable polymeric matrix comprising a mixture of polylactic acid (PLA) and polyglycolic acid (PGA), wherein the PLA:PGA ratio is 50:50, or between 65:35 and 95:5, inclusive; and
   An RNAi (RNA interference) agent incorporated within the biodegradable polymeric matrix, wherein the RNAi agent comprises a sense strand and an antisense strand, wherein the sequences of the sense strand and the antisense strand target a prostate carcinoma gene, and wherein the sequence of the sense strand consists essentially of a sequence selected from the group consisting of SEQ ID NO: 23 (PAPPA), SEQ ID NO: 30 (Brd4), SEQ ID NO: 15 (NETO2), SEQ ID NO: 22 (PTPRA), SEQ ID NO: 21 (PTPRA).

2. The DDD of claim 1, wherein the DDD comprises at least one additional RNAi agent targeting at least one additional gene sequence selected from the group consisting of: SEQ ID NO: 5 (BMI1), SEQ ID NO: 6 (BMI1), SEQ ID NO: 14 (NETO2), SEQ ID NO: 15 (NETO2), SEQ ID NO: 25 (PAPPA), SEQ ID NO: 23 (PAPPA), SEQ ID NO: 20 (PTPRA), SEQ ID NO: 22 (PTPRA), SEQ ID NO: 21 (PTPRA), SEQ ID NO: 19 (PTPRA), SEQ ID NO: 31 (Brd4), SEQ ID NO: 30 (Brd4), SEQ ID NO: 33 (EZH2), SEQ ID NO: 17 (gp130), SEQ ID NO: 27 (ErbB3), SEQ ID NO: 29 (PSCA), SEQ ID NO: 1 (Androgen receptor), SEQ ID NO: 4 (Androgen Receptor), SEQ ID NO: 3 (Androgen Receptor), and SEQ ID NO: 13 (hTERT).

3. The DDD of claim 1, wherein said DDD further comprises an RNAi agent targeting a gene selected from the group consisting of EGFR, VEGF, and AURKB.

4. The DDD of claim 1, wherein the sense and the antisense strands of the RNAi agent each have a dTdT overhang at the 3'-end.

5. The DDD of claim 1, wherein the RNAi agent is chemically modified with a modification selected from the group consisting of 2'-O-methyl (2'-OMe), 2'-O-(2-methoxyethyl) (MOE) and 2'-fluorine.

6. The DDD of claim 1, wherein the RNAi agent is conjugated to a molecule selected from the group consisting of a cholesterol moiety, spermine, hydrophobized hyaluronic acid-spermine conjugates (HHSCs), alpha-tocopherol-vitamin E, and a cell penetrating peptide; or is complexed with a cationic molecule.

7. The DDD of claim 1, wherein the biodegradable matrix further comprises 5%-12% mannitol.

8. The DDD of claim 1, wherein the PLA and PGA are present in a ratio of between 80:20 and 90:10, inclusive, and the polymer has a molecular weight of greater than 50 KDa.

9. The DDD of claim 1, further comprising a pH-modulating additive.

10. The DDD of claim 1, further comprising 0.5%-5%, or 10% trehalose.

11. The DDD of claim 1, further comprising a coating comprising an additional biodegradable polymer.

12. The DDD of claim 1, further comprising a therapeutic agent selected from the group consisting of a small-molecule therapeutic agent, a chemotherapy agent, and an immunotherapy agent against prostate carcinoma.

13. The DDD of claim 1, wherein 95% of the RNAi agent is released from the DDD over a time period between 3-24 months, inclusive.

14. The DDD of claim 1, wherein less than 50% of the RNAi agent is released from the DDD over a time period of 1 month starting from implantation.

15. The DDD of claim 1, wherein less than 75% of the RNAi agent is released from the DDD over a time period of three months starting from implantation.

16. A method of treating a prostate carcinoma in a subject, comprising the step of implanting the DDD of claim 1 into the prostate of the subject, thereby treating a prostate carcinoma.

17. The method of claim 16, wherein the DDD's are implanted into the subject via an apparatus selected from the group consisting of ultrasound apparatus and a seed implantation prostate brachytherapy apparatus, using a needle.

18. The method of claim 16, wherein the number of DDDs per treatment is determined to achieve a dose of 0.008-0.065 mg/kg/month.

* * * * *